(12) United States Patent
Paolitto et al.

(10) Patent No.: US 6,416,470 B2
(45) Date of Patent: Jul. 9, 2002

(54) SURGICAL RETRACTOR HAVING LOW-FRICTION ACTUATING MEANS AND CONTOURED BLADE ARMS

(75) Inventors: Anthony Paolitto, St. Leonard; Giovanni Mannarino, Montreal; Valerio Valentini, Montreal; Bruno Zoccali, Montreal; Raymond Cartier, Town of Mount Royal, all of (CA)

(73) Assignee: Coroneo, Inc., Montreal (CA)

( * ) Notice: Subject to any disclaimer, the term of this patent is extended or adjusted under 35 U.S.C. 154(b) by 0 days.

(21) Appl. No.: 09/740,001

(22) Filed: Dec. 20, 2000

(30) Foreign Application Priority Data

Jun. 26, 1998 (CA) ................................................ 2237877

(51) Int. Cl.[7] .............................................. A61B 17/02
(52) U.S. Cl. ........................................ 600/232; 600/233
(58) Field of Search ................................. 600/232, 206, 600/210, 233, 231, 215, 209, 227, 229

(56) References Cited

U.S. PATENT DOCUMENTS

| | | | | |
|---|---|---|---|---|
| 5,067,477 A | * | 11/1991 | Santangelo | 600/232 |
| 5,167,223 A | | 12/1992 | Koros et al. | |
| 5,967,972 A | * | 10/1999 | Santilli et al. | 600/232 |
| 6,099,468 A | * | 8/2000 | Santilli et al. | 600/232 |
| 6,102,854 A | * | 8/2000 | Cartier et al. | 600/210 |
| 6,206,828 B1 | * | 3/2001 | Wright | 600/232 |
| 6,231,506 B1 | * | 5/2001 | Hu et al. | 600/210 |

FOREIGN PATENT DOCUMENTS

EP            0 411 586 A1         2/1991

* cited by examiner

Primary Examiner—Pedro Philogene

(57) ABSTRACT

A retractor for performing surgery, for instance cardiac surgery on the coronary organs of a patient, which has a driving member to which the surgeon input is applied in the form of a mechanical force or torque, a thoracic structure engaging member which interfaces and retracts the patient's thoracic structure when surgeon input is applied to the movable driving member, and a surgeon input load-reducing and load-normalizing mechanism provided in at least one mechanical interface between retractor components where relative motion therebetween occurs. The load-reducing and load-normalizing mechanisms are preferably non-lubricated, thereby tending to ensure an inert and sterile environment during surgery. The retractor is comprised of a locking arrangement allowing a retractor spreader arm to be secured at any longitudinal position along the rack bar, independently of the pinion's position. The thoracic retractor according to this invention tends to improve the efficiency and safety of surgery by reducing the surgeon input required to achieve retraction, and by allowing said input to be applied more uniformly and in a controlled manner free from sudden movements through the normalization of retractor variables.

21 Claims, 21 Drawing Sheets

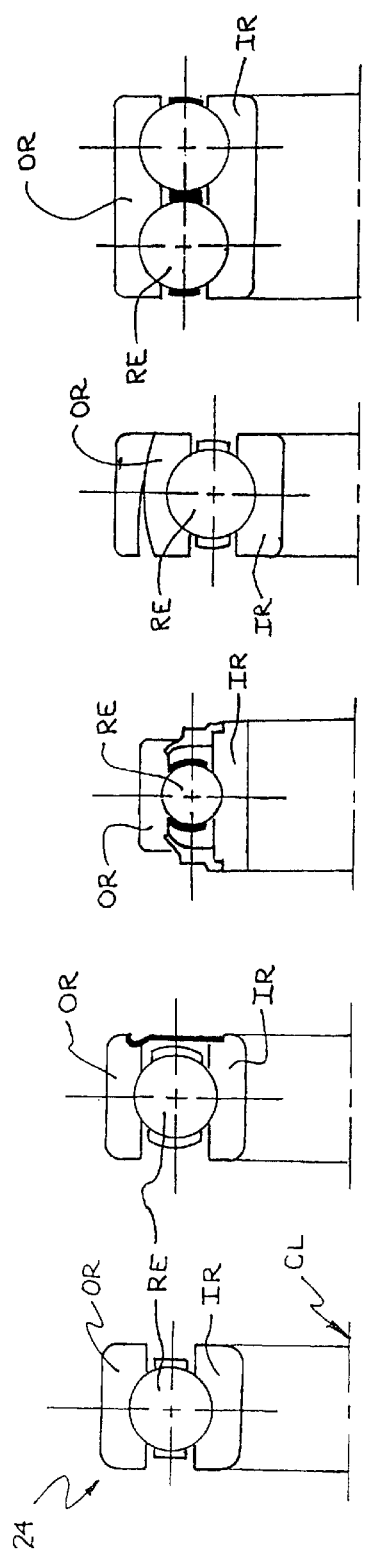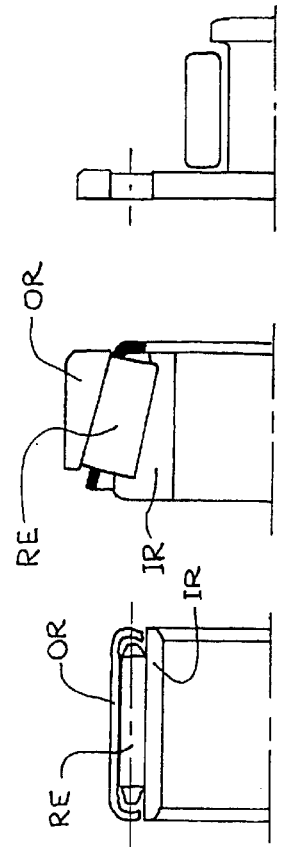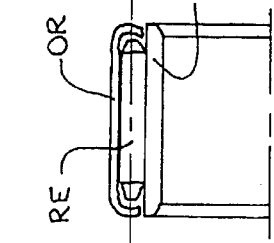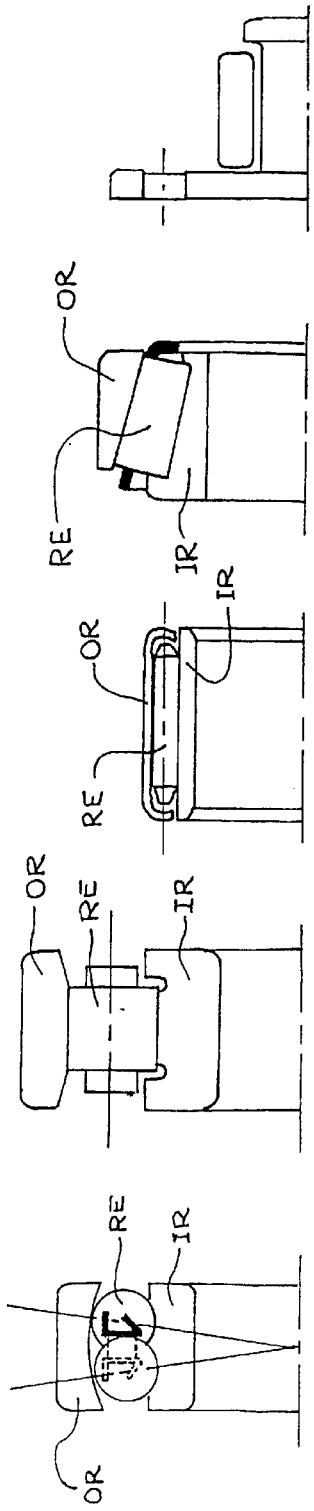

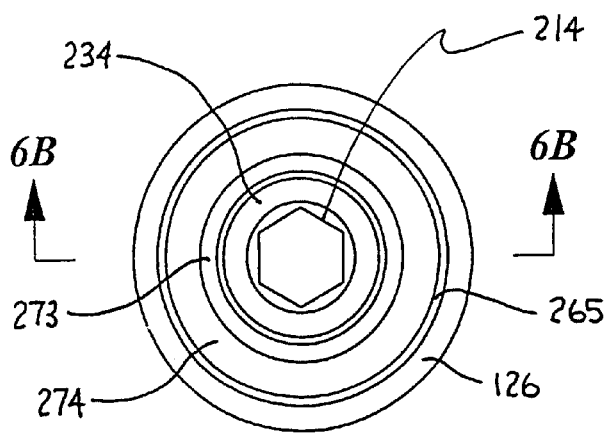
*Figure 6A*
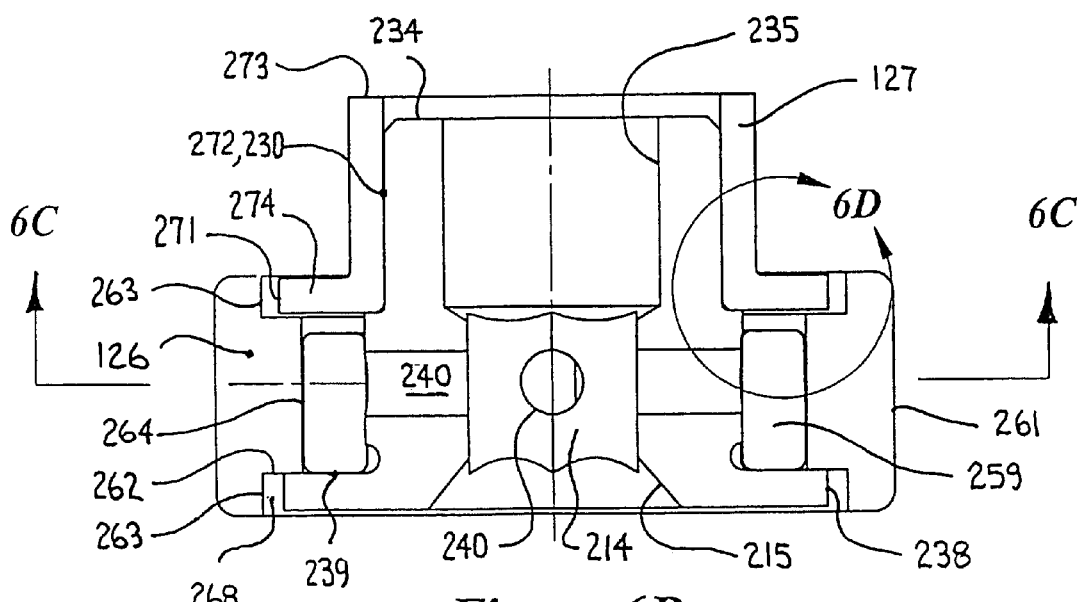
*Figure 6B*
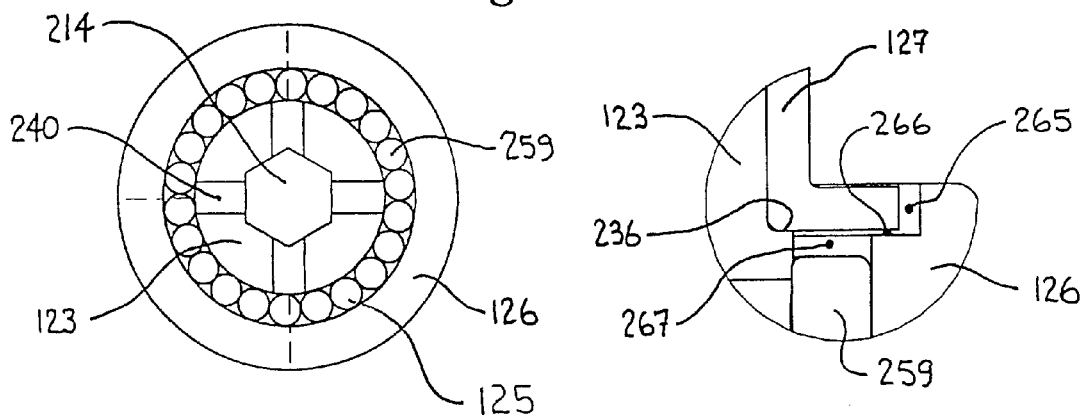
*Figure 6C*     *Figure 6D*

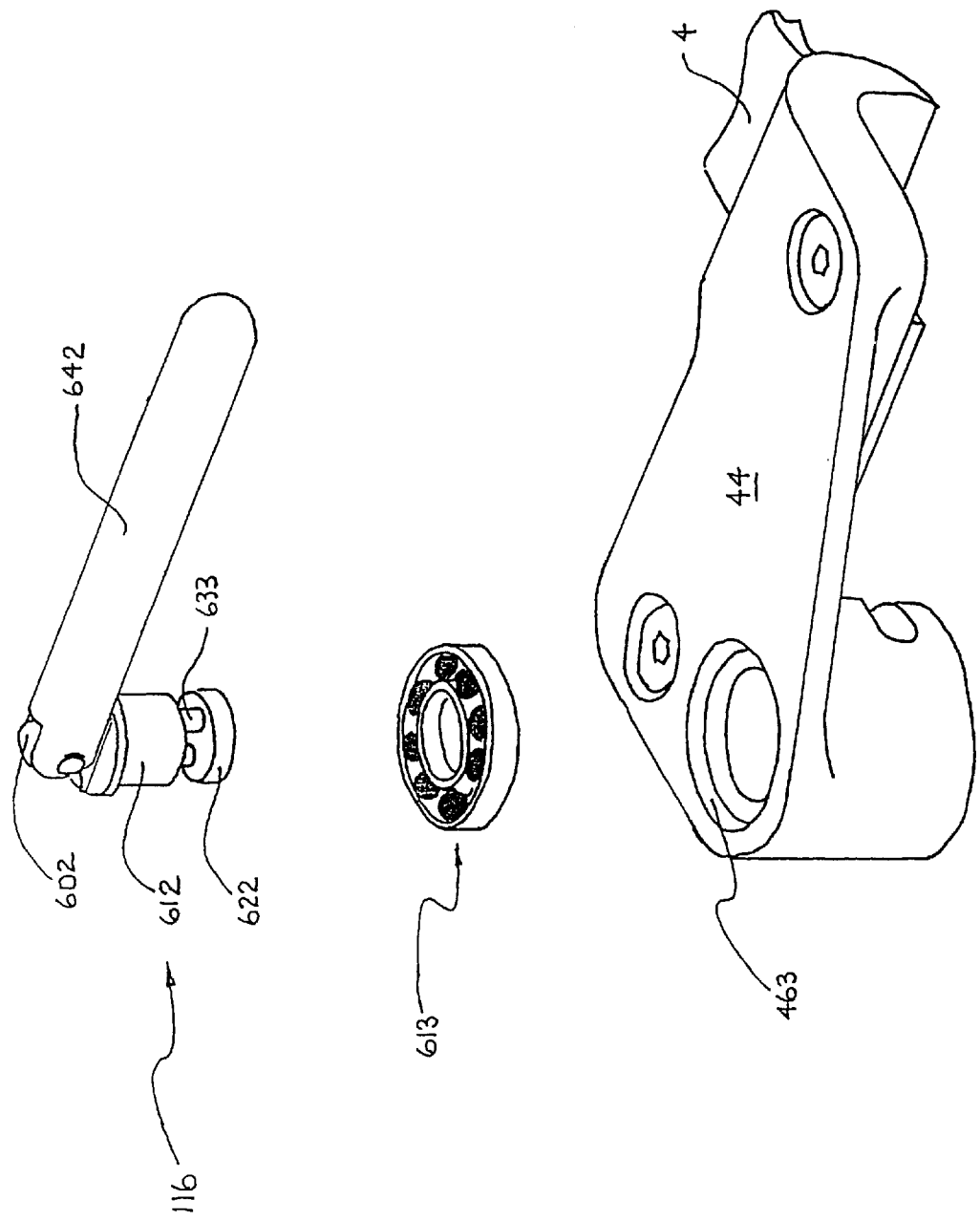

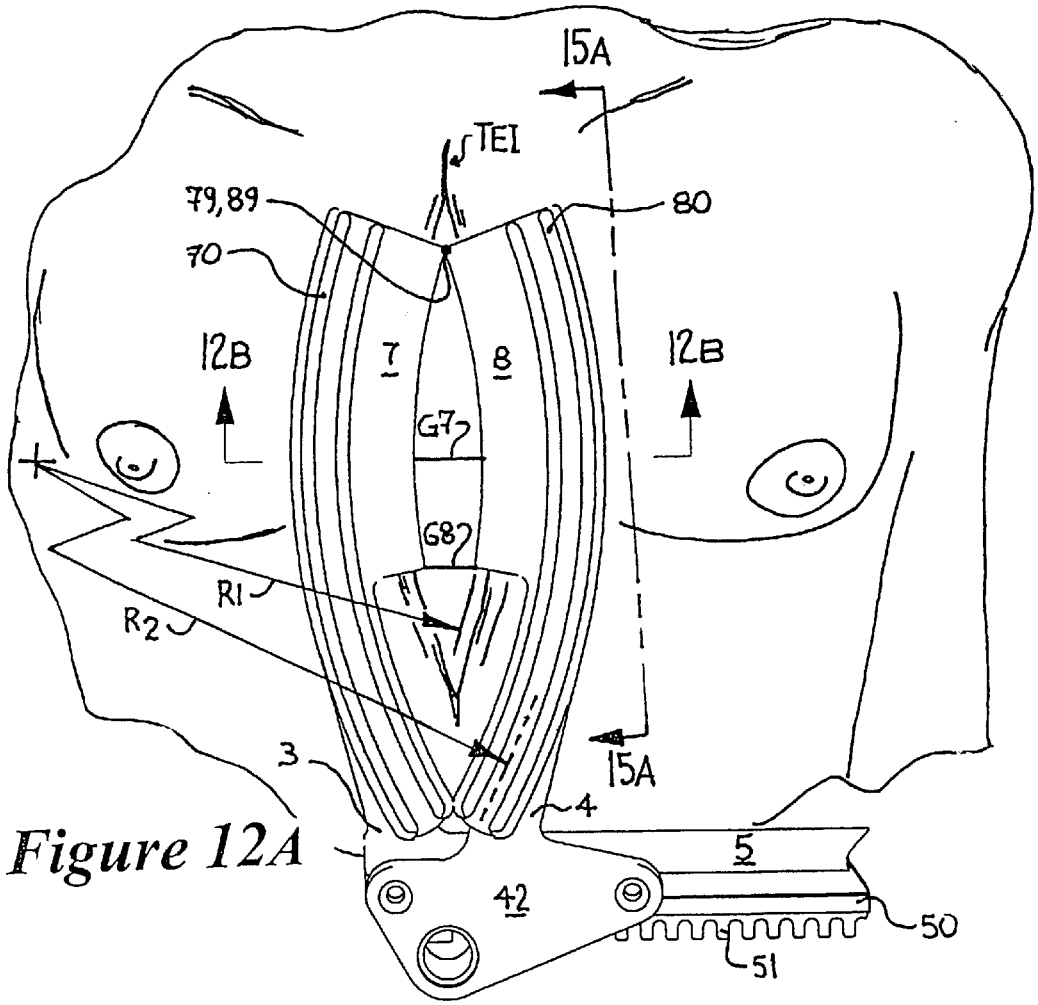
Figure 12A
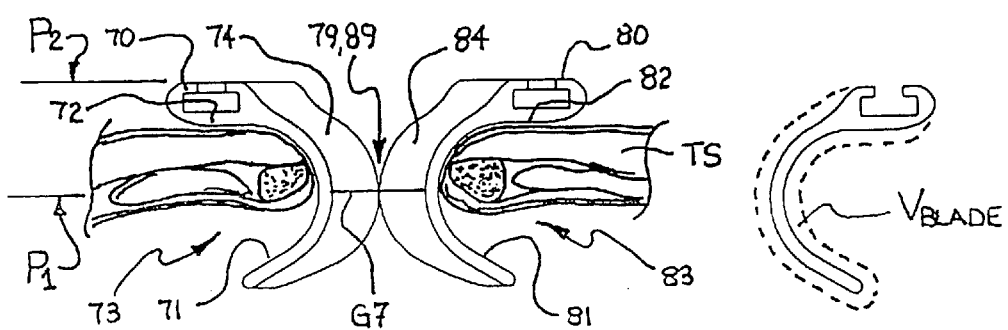 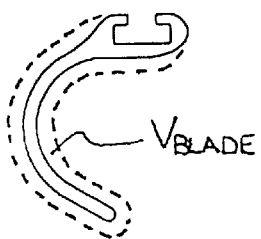
Figure 12B  Figure 12C

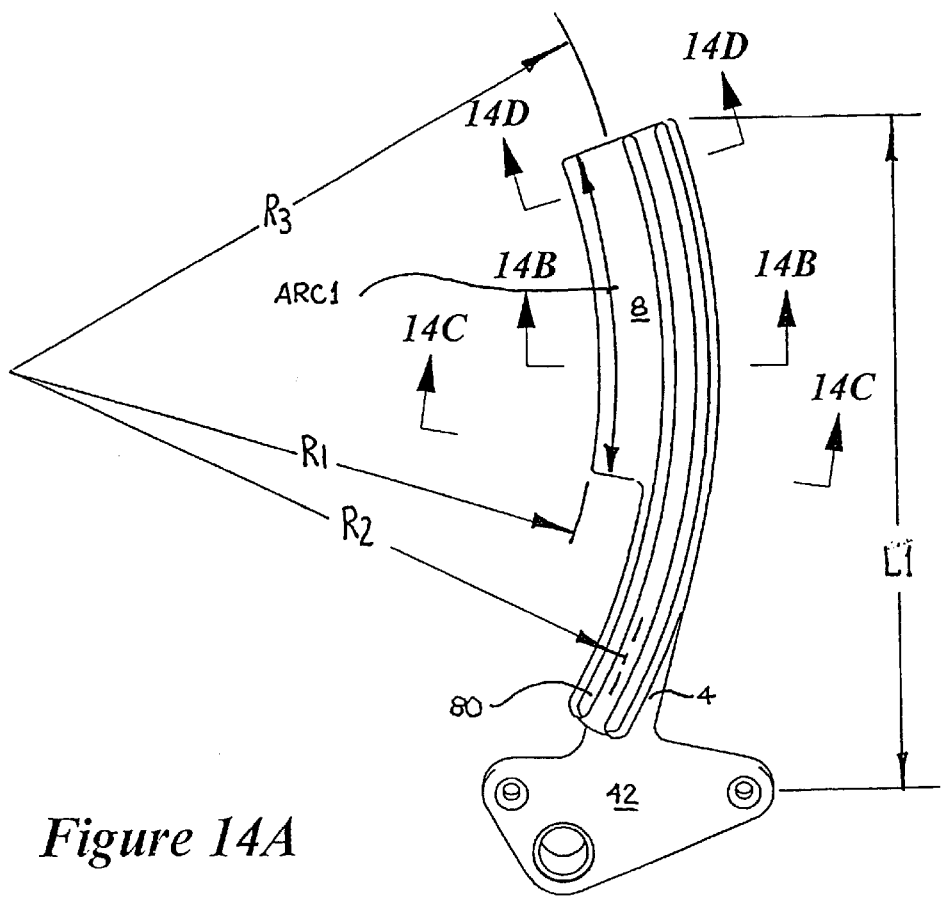
Figure 14A
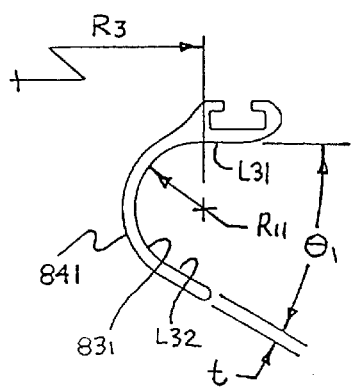 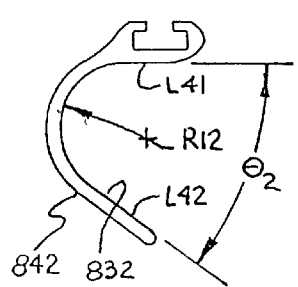 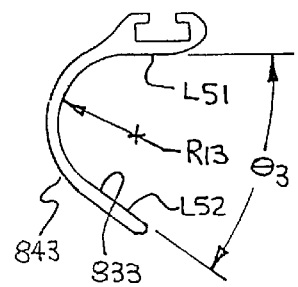
Figure 14B  Figure 14C  Figure 14D

SURGICAL RETRACTOR HAVING LOW-FRICTION ACTUATING MEANS AND CONTOURED BLADE ARMS

CROSS REFERENCE TO RELATED APPLICATIONS

This application is a continuation of international PCT/CA99/00593 filed on Jun. 25, 1999 and designating the U.S.

FIELD OF THE INVENTION

The present invention relates to the field of surgical apparatus and more specifically, to retractors used in surgery.

BACKGROUND OF THE INVENTION

Retractors of all shapes and sizes have been present since the dawn of surgery. A common type of retractor is the chest retractor or thoracic retractor. Retractors of this category may comprise sternum retractors, thoracotomy retractors, mini-thoracotomy retractors, mini-sternotomy retractors, and retractors used for the surgical harvesting of internal thoracic arteries through a sternotomy or intercostal approach incision. For instance, such internal thoracic arteries may comprise the left internal mammary artery.

Sternum retractors are commonly used in cardiac surgery. Cardiac surgery may take several forms. For instance, these forms include traditional coronary artery bypass graft surgery (CABG) requiring the heart-lung machine, CABG surgery performed directly on a beating heart, minimally invasive direct coronary artery bypass surgery (MIDCAB), heart valve repair surgery, heart valve replacement surgery and surgery to correct a septal wall defect, whether atrial or ventricular. Thoracic retractors serve to incise, penetrate and retract the thoracic structure, namely the surface, underlying tissue and bone structure of a patient, in order to access the body organs and internal body tissue contained within the patient's thorax. In the case of a sternum retractor, the thoracic structure in question is the patient's sternum and entire ribcage. The body organs and internal body tissue exposed by use of a sternum retractor will comprise the coronary organs, which include in particular the heart, the heart's arteries and veins, the surrounding tissue and vessels, the pericardium, the thymus, the pleura, and any other tissue within the mediastinum or the space between the two lungs. Sternum retractors are typically used in CABG surgeries or valve replacement surgeries.

The drive in recent years for less invasive cardiac surgery has resulted in smaller chest incisions and consequently smaller chest retractors as well. In minimally invasive cardiac surgery, such as MIDCAB, mini-thoracotomy retractors were introduced to laterally retract a pair of adjacent ribs and expose the underlying coronary organs through the resultant intercostal space.

Most known chest retractors have an elongate rack bar and two retracting arms, namely a fixed retracting arm and a movable retracting arm. Both arms typically extend in a direction substantially normal to the rack bar. The movable arm can be displaced along the rack bar using a crank, which also acts as a torque lever, to activate a pinion mechanism. Two blades are provided, usually below the retractor arms, to interface with the patient's sternum or skin, and which forms part of the thoracic structure. The basic design and mechanism for separating the two or more spreader members or retractor arms of chest retractors have remained relatively unchanged since the first introduction of retractors in cardiac surgery. Consequently, cardiac surgeons have developed a manual proficiency in using the current retractors.

In all chest retractors, there is a resistance to retraction by the patient's thoracic structure and by the retractor itself, which the surgeon must overcome in deploying the retractor to expose the coronary organs. The separating force the surgeon applies is mainly a function of the geometry of the rack and pinion mechanism, the length of the retractor arm, and the friction at the interface between all moving components in the retractor assembly. The separating force to overcome the resistance load on the retractor may at times be excessive since:

a patient may be very corpulent;

a patient's bones may be very brittle, and therefore especially resistant to rotation of the ribs about the spine;

the retractor blade design may result in concentrated loads being generated at locations remote from the rack bar and pinion mechanism;

friction in the retractor system may be high; and wear may have occurred at the mechanical interface between moving components.

The deployment of the retractor, and more specifically the relative movement of the retractor arms, may at times be intermittent, or "jerky" and not smooth, since:

the thoracic structure generally imposes variable loads on the retractor as a function of its retracted opening;

the meshing of the crank and pinion mechanism of the retractor may not be continuous, such that the load at the crank handle may vary as a function of the pinion position within the rack grooves and consequently as a function of the circumferential orientation of crank handle;

the load to overcome friction between retractor components to set retraction in motion is typically higher than the load to keep said components in motion;

friction between moving retractor components may be subject to variation given uneven wear in components; and the friction forces associated with the operation of the retractor are normally linked to the resistance force exerted by the thoracic structure, which is itself variable as a function of its retracted opening.

In most chest retractors, the pinion mechanism usually consists of two pins which engage the rack teeth within grooves formed therebetween in a variety of orientations depending on the rotation of the pinion assembly (and the crank handle usually attached to the pinion assembly). This results in a substantially stable orientation when both pins are engaged with the rack teeth, and a substantially unstable orientation when only one pin is engaged with a rack tooth. This also results in an alternation of discrete and substantially stable locked positions with unstable unlocked positions of the retractor arms along the entire length of the rack.

Based on the foregoing, it would therefore be advantageous to provide a surgical retractor, for instance a sternum retractor, with easier deployment in cardiac surgery.

Thus, it is one object of the present invention to attempt to reduce the separating force and torque the surgeon must apply to the retractor, to effect retraction in surgery.

It is a further object of the present invention to seek to maintain more uniform separating loads by normalizing the variables in chest retractor design discussed above and experienced during deployment in surgery.

It is a further object of the present invention to aim to reduce the risk of injury to a patient by providing improvements to retractors, for instance sternum retractors, that allow the surgeon to deploy said retractors in a controlled manner free from sudden or intermittent movements.

It is a further object of the present invention to provide a chest retractor, for instance a sternum retractor, which may more readily be cleaned and sterilized.

It is a further object of the invention to provide a retractor design which is intended to reduce concentrated loads sometimes found at the extremities of a surgical incision, when compared to certain prior art retractors, and for a given retracted opening in the thoracic structure when measured at the mid length location along the incision.

It is a further object of the present invention to provide a chest retractor with contoured retractor blades adapted to more closely conform to the ribcage halves along a sternotomy incision as the thoracic structure is retracted.

It is an additional object of the present invention to provide a retractor having a continuous variable range of lockable open retracted positions.

It is an additional object of the present invention to retrofit existing retractors, for instance sternum retractors, with improvements that aim to reduce and normalize separating loads which the surgeon must apply during retraction of the thoracic structure therewith.

It is an additional object of the present invention to apply the concepts and principles of this invention, as they relate to chest retractors and more specifically to sternum retractors, to other types of retractors.

These and other objects of the present invention will become apparent from the description of the present invention and its preferred embodiments which follows.

SUMMARY OF THE INVENTION

According to one broad aspect of the present invention, there is provided a surgical retractor having an elongate guide member, and having first and second spreader arms each extending substantially transversely of the guide member and each extending therefrom generally in the same direction, the first and second spreader arms being disposed generally parallel to each other, the first spreader arm being movable along the length of the guide member from a first position, wherein the spreader arms are adjacent one another, to a second position, wherein the spreader arms are spaced apart from one another, to thereby effect retraction of a surgical incision; characterized in that the surgical retractor comprises: an actuator for effecting said movement of the first spreader arm, the actuator being operatively connected to the guide member and to the first spreader arm, and wherein the actuator is translatable along the length of the guide member; and a low friction interfacing member, the low friction interfacing member being disposed between the actuator and the guide member at a point of contact of said actuator with said guide member.

With reference to preferred embodiments of the invention, the low friction interfacing member may advantageously be connected either to a pinion mechanism housing or be inserted in a slider slot provided along the length of a corresponding rack bar. The low friction interfacing member is preferably of an open configuration which tends to facilitate sterilization and easy cleaning of blood products from constituent elements prior to sterilization. As well, the low friction interfacing member is preferably non-lubricated tending to ensure inert and sterile environment during surgery.

The thoracic retractor may also advantageously provided with a pinion arrangement having a friction reducing member. As well, the driving member therefor may be provided with a friction reducing member such as a bearing.

The retractor may also comprise a locking arrangement to allow the adaptor to be secured at any longitudinal position along the rack bar, independently of the pinion's position.

A low friction interfacing member according to the present invention may also be used as a retrofit arrangement for existing retractors.

The pinion arrangement preferably comprises two pinions, but those skilled in this art will appreciate that more pinions may also be provided.

All the foregoing features contribute to attempt to optimize the operation and safety of the retractor.

The retractor according to the present invention seeks to reduce the separating force and torque which the surgeon must apply at the driving member of the retractor and thereby tends to facilitate its deployment. As well, the retractor of the present invention attempts to substantially normalize retraction loads; that is, it is intended to allow the surgeon to sense more uniform loads and to thereby result in a steadier deployment of the retractor throughout its open range. Since a jerky deployment of the retractor can lead to sudden retraction movements, normalization may result in less risk of inadvertent tissue trauma or sternum fracture. Thus the present invention describes a low-friction interfacing member for providing load reduction and load normalization in thoracic retractors.

In surgical interventions which obtain access to the coronary organs via a midline sternotomy incision, the nature of the surgical incision is substantially linear since the sternum or breastbone is cut in two. The patient's thoracic structure usually imposes the greatest resistance to retraction at the extremities of the surgical incision, where tearing of tissue most often occurs. This also tends to result in the highest concentration of resistance load being applied to the retractor arms at the free ends thereof, namely at the extremity of the incision location which is furthest away from the rack and pinion mechanism of the retractor. The retractor of this invention, with its arcuate spreader arms and contoured thoracic structure engaging members is expected to reduce these concentrated loads at the incision extremities for a desired retracted opening in the thoracic structure at the mid length location along the surgical incision. This would therefore be advantageous since the overall separating force the surgeon must apply will also be reduced for a given opening in the thoracic structure.

In retracting a patient's thoracic structure subsequent to a midline sternotomy, the two halves of the ribcage do not have a tendency to spread apart in a parallel orientation along the sternotomy incision. The top portion of the ribcage tends to go from a generally cylindrical-shaped surface, when the incision is not retracted, to a generally barrel-shaped surface when the incision is retracted. That is, the center portion of the ribcage along the sternotomy incision retracts more readily in an outward and upward direction than the extremities of the incision, which are somewhat restricted by the endpoints thereof at the patient's abdomen and collarbone. This forms a lens-shaped opening for the retracted incision. Many prior art retractors do not accommodate this barrelling behaviour. The retractor of this invention, with its contoured thoracic structure engaging members that interface with the two halves of the patient's incised sternum and that conform closely to this non-parallel barrelling of the ribcage halves along the sternotomy incision during retraction, would offer advantages in tending to minimize the likelihood of sternal breakages and induced tissue trauma.

BRIEF DESCRIPTION OF THE DRAWINGS

For a better understanding of the present invention and to show more clearly how it may be carried into effect, reference will now be made by way of illustration and not of limitation to the accompanying drawings, which show an apparatus according to preferred embodiments of the present invention and in which:

FIGS. 4A to 4J illustrate top cross-sectional halves of bearing variants, about their respective centerlines, which may be adapted as the load-reducing and load-normalizing mechanism of FIG. 1B;

FIGS. 6A to 6D illustrate assembled views of the load-reducing and load-normalizing mechanism of FIG. 5;

FIG. 9 is an exploded perspective view illustrating a fifth embodiment according to this invention, comprising a friction-reducing member for the pinion mechanism of the sternum retractor of FIG. 1A;

FIG. 12A is a top anterior view of the patient's thoracic structure engaged with arcuate blades of the sternum retractor of FIG. 1A prior to retraction of the thoracic structure, illustrating an eighth embodiment according to this invention;

FIG. 12B is a cross-sectional view through the patient's thoracic structure and through the sternum retractor of FIG. 12A, illustrating the engagement of the thoracic structure in its cylindrical-like configuration prior to retraction with respective concave surfaces of the arcuate blades thereof;

FIG. 12C is a cross-sectional view of a spreader arm and blade of the sternum retractor of FIG. 1A;

FIG. 14A is a top view of an arcuate spreader arm for the sternum retractor of FIG. 1A;

FIG. 14B to 14D illustrate various sectional views along the arcuate spreader arm of FIG. 14A, taken along the portion of the spreader arm which is configured with an underlying blade;

DETAILED DESCRIPTION OF THE INVENTION

Figure 1A:
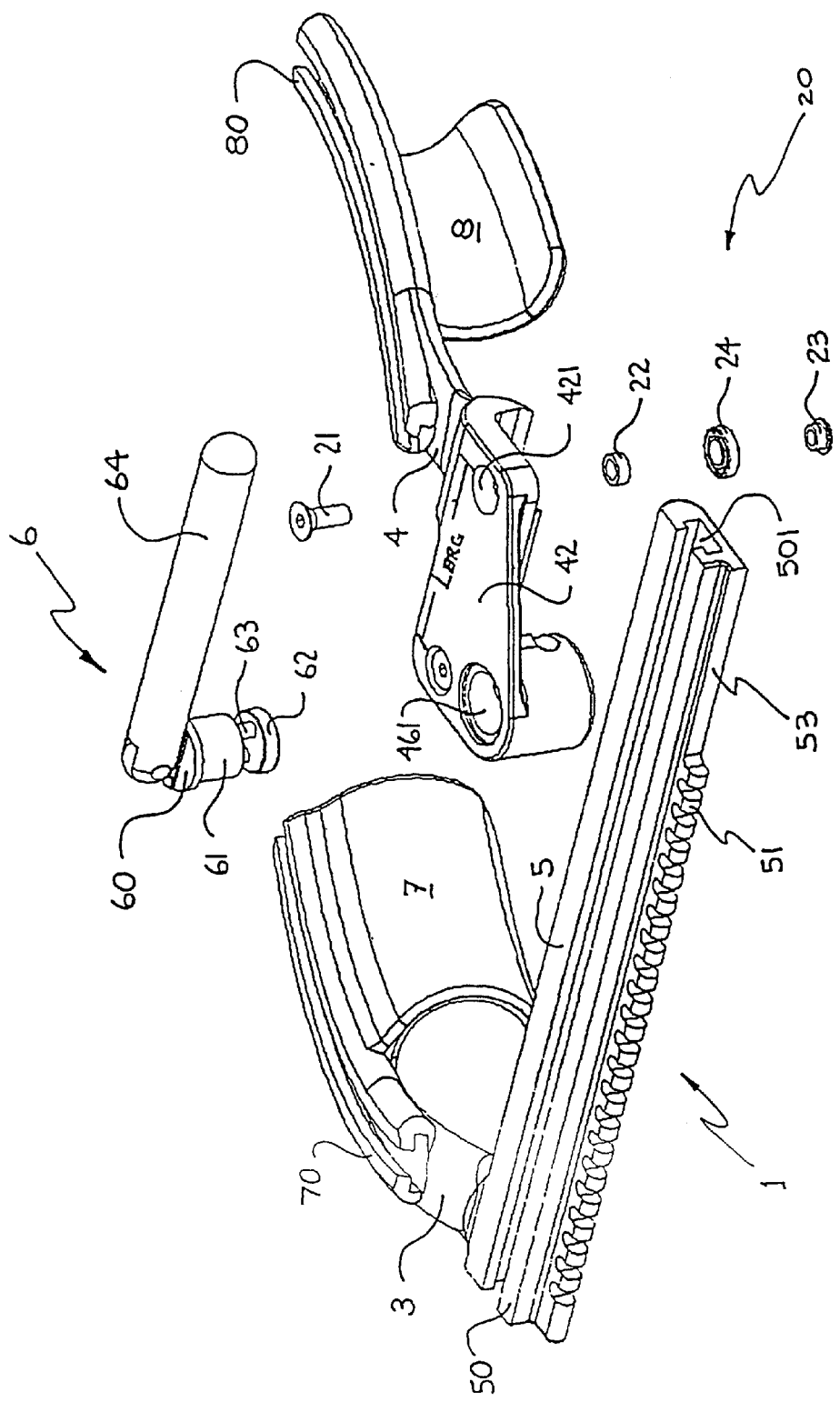
FIG. 1A is an exploded perspective view illustrating a low friction interfacing member, also termed a load-reducing and load-normalizing member, for a sternum retractor, all according to a first embodiment of the present invention.

The description which follows, and the embodiments described therein, are provided by way of illustration of an example, or examples, of particular embodiments of the principles of the present invention. These examples are provided for the purposes of explanation, and not of limitation, of those principles and of the invention. In the description which follows, like parts are marked throughout the specification and the drawings with the same respective reference numerals. The drawings are not necessarily to scale and in some instances proportions may have been exaggerated in order to more clearly depict certain features of the invention.

The features and principles of this invention can be applied, in whole or in part, to many types of retractors, and more particularly to chest retractors utilized in cardiac surgery. The description of the preferred embodiments will be illustrated with respect to sternum retractors, for instance those used to perform multiple vessel CABG surgery and valve surgery through a midline sternotomy incision.

In part, the preferred embodiments of this invention will introduce enhancements and additional features to a retractor described in copending Canadian patent application Serial No. 2,216,893 filed on Sep. 30, 1997 in the names of Cartier and Paolitto and entitled "Sternum Retractor for Performing Bypass Surgery on a Beating Heart", the contents of which are incorporated herein by reference. This existing application has been assigned to CoroNéo Inc., the assignee of the present application.

By way of a general overview, FIG. 1 illustrates an exploded view of the chest retractor apparatus according to a preferred embodiment of the present invention. The sternum retractor 1 includes five major parts: (i) a guide member such as an elongated rack bar 5, (ii) first and second retractor spreader arms 3 and 4, with one retractor spreader arm 3 being preferably fixed to the rack bar 5 and the other retractor spreader arm 4 being preferably movable with respect to the rack bar 5, (iii) an actuator for effecting movement of the retractor spreader arm 4, which preferably comprises a pinion mechanism 6, and (iv) a low-friction interfacing member in the nature of a friction-reducing, or a load-reducing and load-normalizing mechanism 20.

Retractor arms 3 and 4 extend in a direction substantially transversely with regard to the rack bar 5, extend generally in the same direction therefrom and in parallel orientation with respect to one another. The retractor arms 3 and 4 have a generally arcuate orientation as explained in greater detail herebelow. The movable arm 4 can be displaced along the rack bar 5, and relative to the other arm 3, preferably through rotation of a pinion mechanism 6 activated by the surgeon through crank 64. The actuator is operatively connected to the rack member and to the spreader arm 4, and is translatable along the length of the rack member. This is preferably achieved by the engagement of pinion mechanism 6 with the rack teeth 51 on rack bar 5 through shaft 60. Two retractor blades 7 and 8 are respectively provided with the retractor spreader arms. Preferably, the retractor blades 7, 8 are disposed below the rack bar 5 when the sternum retractor 1 is deployed on a patient. The retractor blades 7, 8 serve to retract a portion of the thoracic structure, thereby exposing the coronary organs to be operated on. Blades 7 and 8 interface with the two halves of the patient's sternum after the sternotomy incision, and thereby act as thoracic structure engaging members.

The sternum retractor 1 advantageously comprises arcuate rails 70 and 80 along the top of arcuate retractor spreader arms 3 and 4 respectively. A similar linear longitudinal rail 50 may also be configured along the top of rack bar 5. These said rails form a mounting perimeter that advantageously serves to engage a positioning and articulation mechanism utilized to place a variety of heart stabilizers during beating heart bypass surgery, as described in the previously mentioned Canadian patent application Serial No. 2,216,893. Alternatively, the positioning and articulation mechanism may also be utilized to set a coronary organ contacting member used in cardiac surgery, such as a valve tissue retractor for example. As well, these rails can also be utilized to engage other surgical apparatus, that need to be secured along the perimeter of the chest retractor during cardiac surgery.

In broad terms, a typical example of the surgical procedure for the set-up and deployment of sternum retractor 1 relating to this invention consists of:

a) A full or partial sternotomy incision;
b) Cauterization of any bleeding vessels subsequent to the sternotomy incision;
c) Insertion of sternum retractor blades 7, 8 along the sternotomy incision, preferably with the portion of the blades which are disposed farthest away from the rack 5 being inserted first, and the remaining portion of the blades 7, 8 being progressively introduced into the incision from the base of the incision (closest to the abdomen) towards the top of the incision (closest to collarbone);
d) Rotation of crank 64 to move spreader arms 3, 4 apart from each other and gradually retract the patient's thoracic structure exposing the coronary organs therewithin;
e) Performing the required surgical intervention;
f) Re-adjusting the opening of the retracted thoracic structure during surgery, if required, by rotation of the crank;
g) Closing the patient's thoracic structure after completion of surgical intervention through opposite rotation of the crank;
h) Removal of the sternum retractor;
i) Closing of the surgical incision.

Figure 2A:
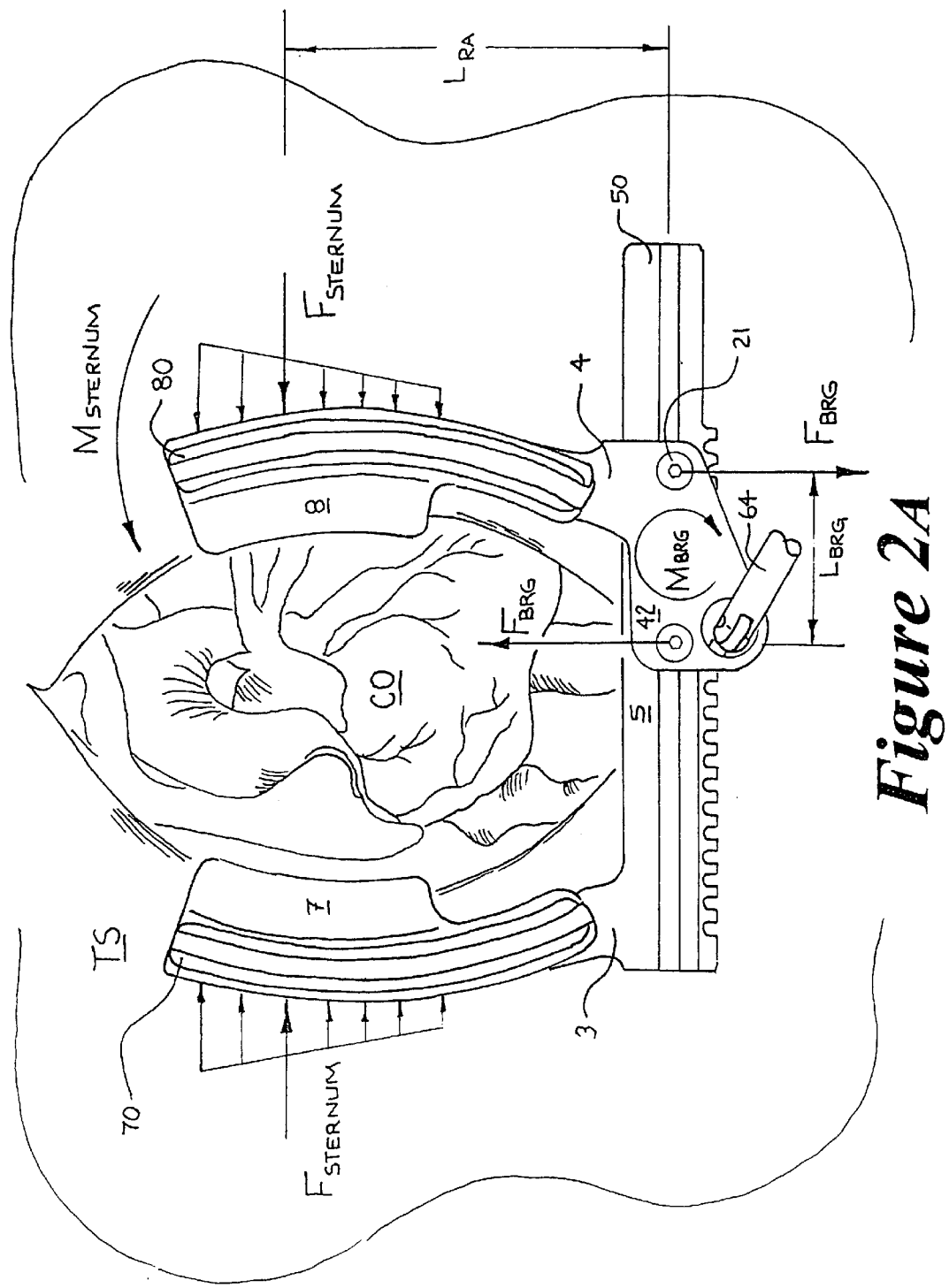
FIG. 2A is a top plan view of the sternum retractor of FIG. 1, schematically illustrating an example of the forces acting on the retractor system.
Figure 2B:
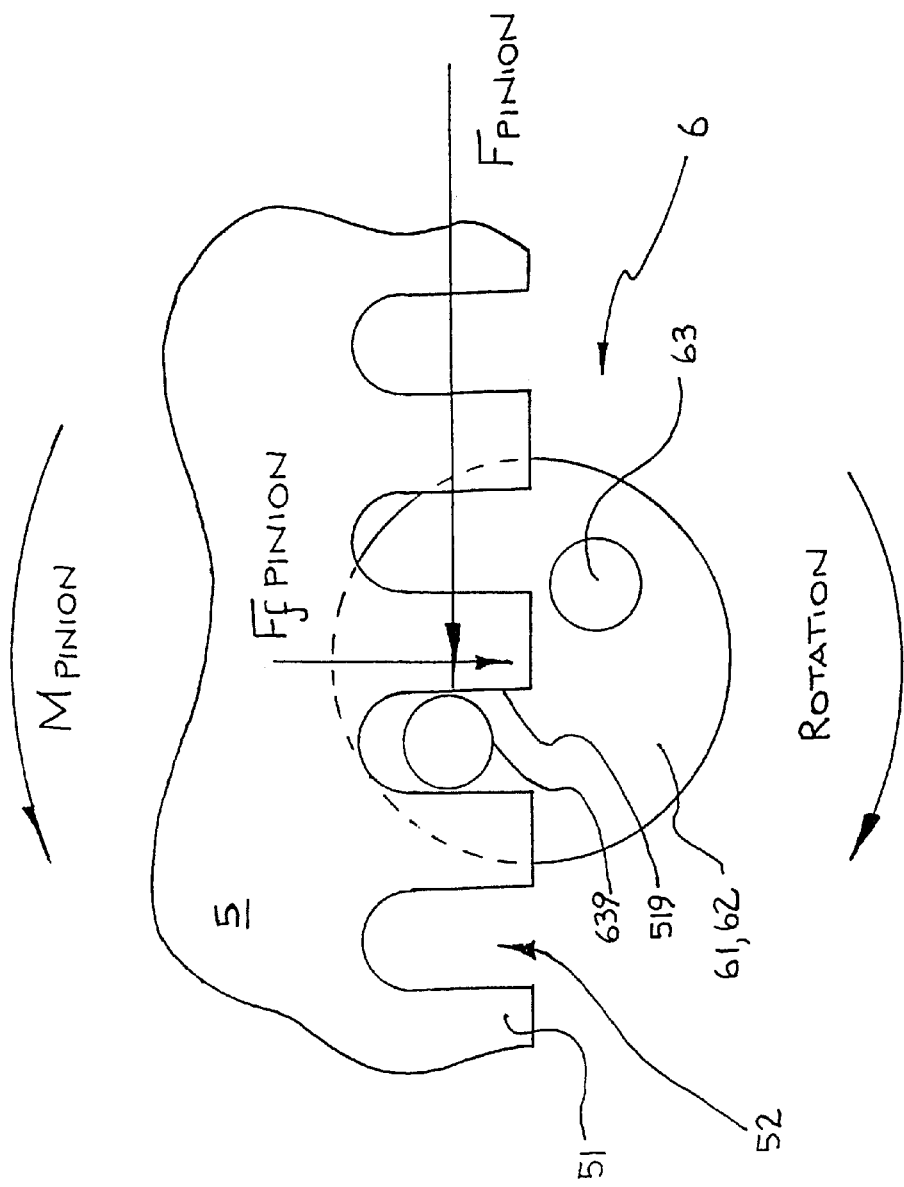
FIG. 2B is a top plan view of a pinion mechanism for the retractor of FIG. 1, with a schematic representation of an example of the forces acting thereon.
Figure 2C:
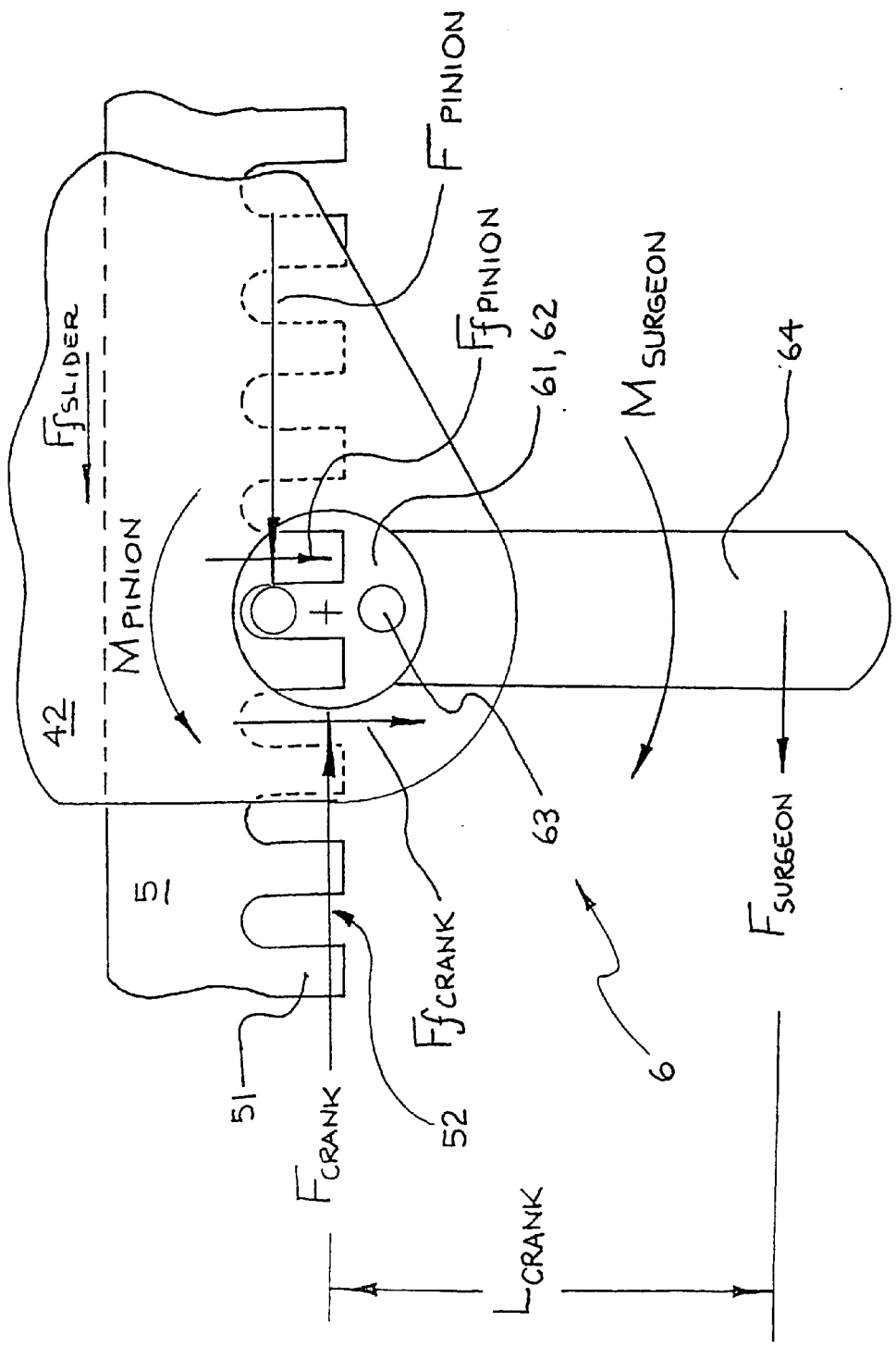
FIG. 2C is a top plan view of the pinion mechanism of FIG. 2B, showing a crank for deployment by a surgeon and an example of the forces the surgeon must apply to the crank to achieve retraction of a thoracic structure.

FIGS. 2A to 2C illustrate schematically examples of the loads exerted by the thoracic structure (labelled TS) on the sternum retractor 1, and the resultant forces within the retractor system. The thoracic structure resists retraction by imposing a load $F_{STERNUM}$ on the blades 7 and 8 of the retractor. The load is distributed along the entire length of the blades. Due to the substantially linear nature of the typical surgical incision, the thoracic structure normally imposes the greatest resistance to retraction at the extremities of the incision, where the tearing of tissue most often occurs. In some patients, where the ribcage is very rigid and not easily rotatable about the spine axis, the maximum load on the retractor blades can be anywhere along the blade's arcuate length depending on the specific patient anatomy. The resultant moment $M_{STERNUM}$, on the retractor, depends on the resistance force $F_{STERNUM}$ exerted on the retractor blades 7 and 8, and also on the length along the retractor arm $L_{RA}$. Thus, $F_{STERNUM}$ schematically represents the distributed resistance load on the retractor blades 7 and 8 concentrated at one location along the blade, and $L_{RA}$ represents the distance between the line of action of $F_{STERNUM}$ and the mechanical interface between spreader arm 3 and 4.

Figure 3:
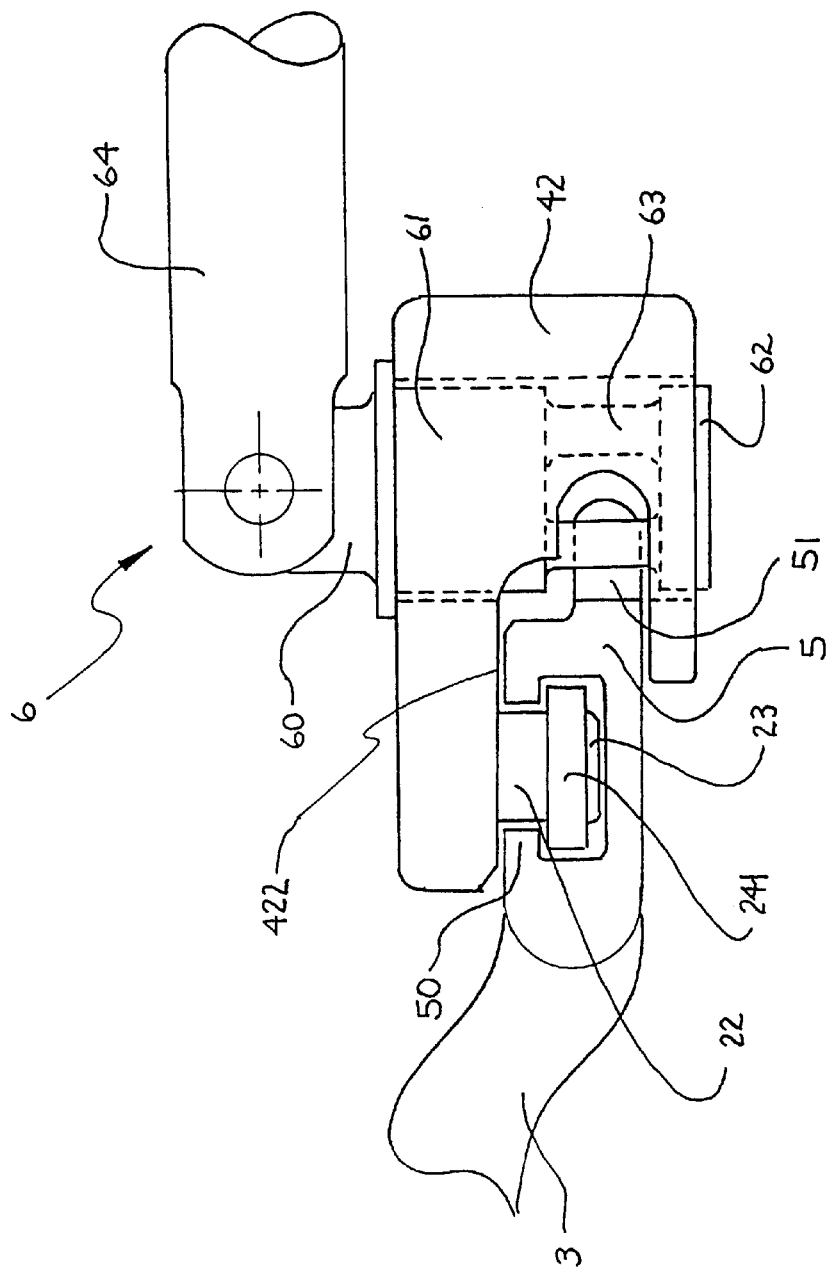
FIG. 3 is a side elevational view of a portion of the retractor of FIG. 1A, illustrating the load-reducing and load-normalizing mechanism of FIG. 1B.

In the specific embodiment shown in FIGS. 1A, 2A and 3, the pinion mechanism 6 is contained in an adaptor in the nature of a crank housing 42. The crank housing 42 is described in greater detail herebelow. Along the rack bar 5 and at the opposing ends of the adaptor 42, the moment $M_{STERNUM}$ is reacted by the forces $F_{BRG}$ and moment $M_{BRG}$, which keeps the retractor arm 4 from rotating towards the retractor arm 3 at their free ends. During translation of retractor arm 4 relative to retractor arm 3 along the rack bar 5, a friction force $Ff_{SLIDER}$ must also be overcome (FIG. 2C). The friction force $Ff_{SLIDER}$ is a function of the coefficient of friction between the two retractor arms; more specifically in the illustrated example, between the rack 5 which is integral with retractor arm 3 and the crank housing 42 which is integral with arm 4. The friction force $Ff_{SLIDER}$ is also a function of the component of force $F_{BRG}$ acting normal to the sliding surface. A wider crank housing 42, with larger spacing $L_{BRG}$, will reduce the magnitude of forces $F_{BRG}$ at the expense of a larger and perhaps heavier retractor, for a given $M_{STERNUM}$.

The force $F_{STERNUM}$ exerted on the retractor blades 7 and 8 is transferred to the rack bar 5, more specifically to rack teeth 51 thereof, and to the pinion mechanism 6 as $F_{PINION}$, for a given $F_{STERNUM}$ as illustrated in the example of FIG. 2B. Depending on the design of the retractor components, $F_{PINION}$ may vary in magnitude. FIG. 2B schematically illustrates the forces exerted from the rack teeth 51 on the pinion member 63. With each half-turn rotation of the crank 64 and simultaneously of the shaft 60, pinion member 63 moves in and out of a slot 52 defined between immediately adjacent rack teeth 51 of rack bar 5, in the case of a dual pinion member arrangement. With the next half-turn rotation, the other pinion member 63 engages an adjacent slot 52 and repeats this motion. Each pinion member 63 engages alternate slots 52 in the rack bar 5 to achieve the relative movement between retractor spreader arms 3 and 4.

As the pinion member 63 moves within a rack slot 52, its perimeter surface 639 rotates and slides relative to the mating surface 519 of the engaged rack tooth 51. A friction force $Ff_{PINION}$ is thereby generated from this relative motion. This friction force is a function of the coefficient of friction between engaged rack tooth 51 and pinion member 63, and the normal component of $F_{PINION}$ to mating surface 519. The friction force $Ff_{PINION}$ may lead to wear at the rack tooth interface and eventually the need for refurbishment or replacement of the retractor.

FIG. 2C illustrates an example of the forces between the pinion mechanism 6 and the retractor arm crank housing 42, and the force and torque the surgeon must provide to retract the thoracic structure through the crank handle 64. The force $F_{PINION}$ on the pinion is reacted by an effective force $F_{CRANK}$ acting between the crank housing 42 and pinion journals 61 and 62 (as best shown in FIG. 3) of pinion mechanism 6. The spacing between pinion members 63 determines the magnitude of $F_{PINION}$ acting between the pinion members and the rack teeth 51, for a given $M_{STERNUM}$. A smaller $F_{PINION}$ is at the expense of a larger tooth pitch rack with coarser travel of retractor arm 4 along the rack bar 5; that is, a larger displacement of movable spreader arm 4 for each revolution of handle 64. The rotation of the pinion mechanism 6 within the crank housing 42 generates a friction force $Ff_{CRANK}$ along the circumference of top pinion journal 61 and bottom pinion journal 62. This may lead to wear at the pinion journal interfaces and eventually the need for refurbishment or replacement of the retractor.

In conventional chest retractors, the surgeon applies force $F_{SURGEON}$ and torque $M_{SURGEON}$ through the crank handle 64, not only to overcome the resistance to retraction $F_{STERNUM}$ of the thoracic structure, but also to overcome the friction forces $Ff_{SLIDER}$, $Ff_{PINION}$ and $Ff_{CRANK}$. The longer the crank length $L_{CRANK}$, the easier is expected to be the surgeon input at the expense of a heavier and perhaps less ergonomic handle. For the purposes of this embodiment, the crank handle 64 is also the movable driving member.

Figure 1B:
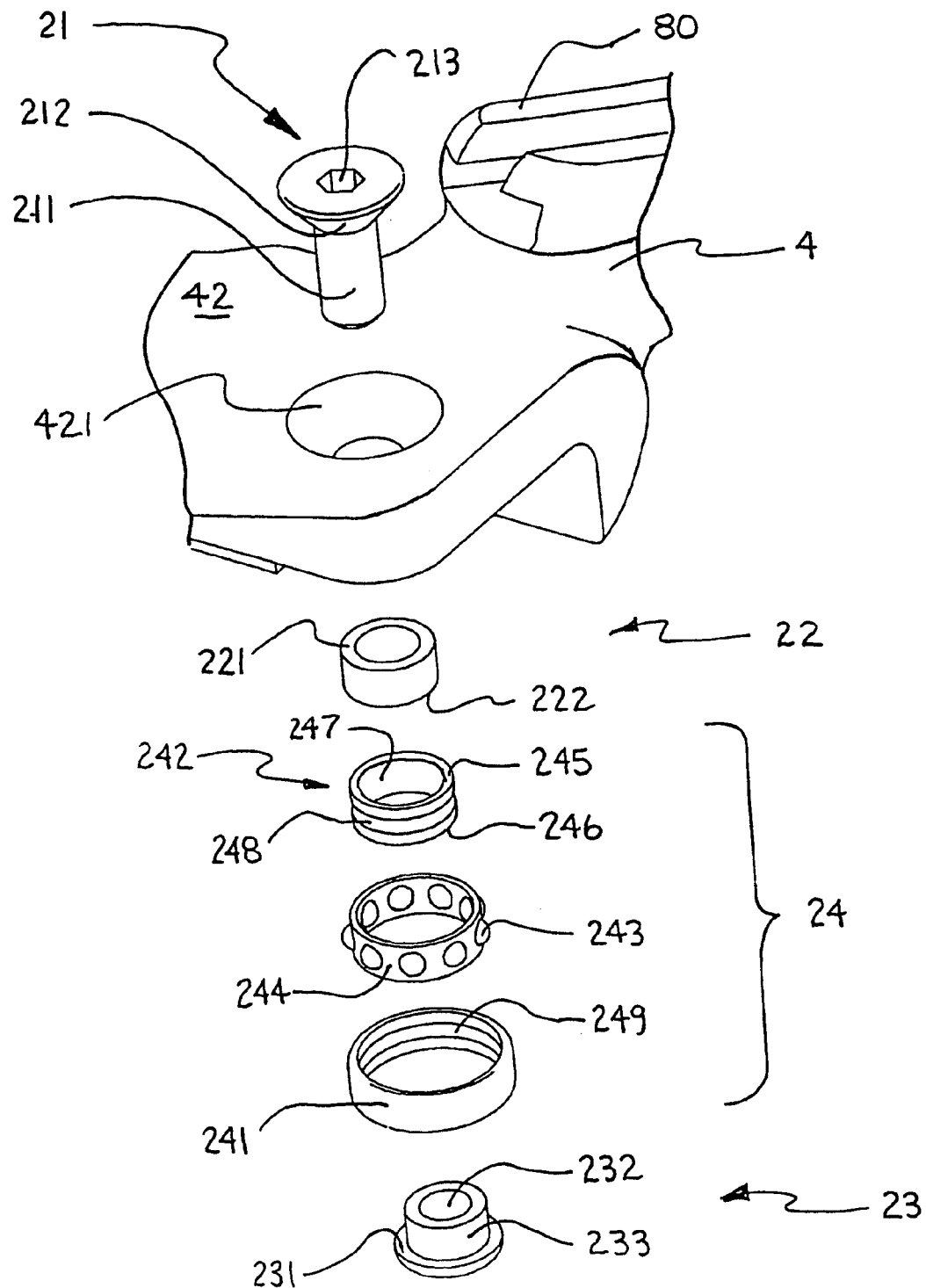
FIG. 1B is an enlarged exploded view illustrating a load-reducing and load-normalizing mechanism of the sternum retractor of FIG. 1A.

As illustrated in FIG. 1A and enlarged in FIG. 1B, a load-reducing and load-normalizing mechanism 20, preferably in the nature of a ball bearing, tends to operate in a fashion to reduce the force $F_{SURGEON}$ and torque $M_{SURGEON}$ required to retract the thoracic structure by overcoming the friction force $Ff_{SLIDER}$. This load-reducing and load-normalizing mechanism 20 will also tend to allow said force and said moment to be applied more consistently and uniformly throughout the retraction range of the apparatus, hence the reference to "load-normalizing" in describing the mechanism.

The load-reducing and load-normalizing mechanism 20 may be comprised of two ball bearings 24 which are each assembled to the crank housing 42, for example, by a screw element 21 and a nut element 23. In FIG. 1A, only the first of the two bearings 24 is shown disassembled. The screw element 21 of the assembled second bearing can be seen engaged within crank housing 42. Both bearings are preferably, but not necessarily, of the same type. The two ball bearings are spaced apart by $L_{BRG}$ such that the force couple $F_{BRG} \times L_{BRG}$ can react the imposed moment $M_{STERNUM}$. This resultant force $F_{BRG}$ between retractor arms 3 and 4 acts through each of the ball bearings 24 of the load-reducing and load-normalizing mechanism 20, through the interface of slider slot 501 of linear rail 50. Thus, a low friction interfacing member is disposed between the actuator and the guide member at a point of contact of the actuator with the guide member.

With reference to FIG. 1B, bearing 24 is comprised of an inner race 242, an outer race 241 and complement of rolling element balls 243 spaced apart circumferentially by a cage 244. The items comprising bearing 24 stay assembled as a whole after fabrication of the bearing, and allow the free rotation of outer race 241 relative to inner race 242 through the complement of rolling element balls 243 that roll within groove 248 in the inner race and groove 249 in the outer race. These grooves 248, 249 also maintain the axial position of the outer race while permitting its free rotation relative to the inner race once the bearing 24 is assembled during fabrication.

The bearing 24 is clamped through its inner race edges 245 and 246 between spacer 22 and nut element 23. Nut element 23 is configured with a pilot diameter 233 to fit into inner diameter 247 of inner race 242. Shoulder 231 of the inner race axially clamps bearing 24 through inner race edge 246 when internal thread 232 becomes engaged with threaded body 211. Spacer 22 is of a tubular configuration to permit screw element 21 to pass through its center and freely engage internal thread 232 of nut element 23. The lateral faces 221 and 222 of spacer 22 contact the underside face 422 of crank housing 42 and inner race edge 245, respectively, when the assembly of mechanism 20 is complete. Screw element 21 is provided with a conical head portion 212 which sits within a corresponding countersink feature 421 in crank housing 42, and threaded body 211 for engaging internal thread 232 in nut element 23. A torque reaction feature 213, a hex drive recess for example, is provided on screw element 21 and nut element 23 (not shown) to enable fastening of the load-reducing and load-normalizing mechanism 20 assembly to the crank housing 42.

Once all components are secured to crank housing 42 by fastening threaded body 211 and nut element 23, only outer race 241 of bearing 24, and rolling element balls 243 along with their cage 244 are free to rotate about the centerline of the load-reducing and load normalizing mechanism 20 assembly. All other components, that is screw element 21, spacer 22, inner race 242 of bearing 24, and nut element 23 are fixed in relation to crank housing 42, and do not rotate.

The pinion mechanism 6 is insertable in the crank housing 42, where the top pinion journal 61 and bottom pinion journal 62 can rotate within port surface 461 (FIG. 1A). It is preferable to have the free terminal end 53 of the rack bar configured without any rack teeth, to enable the insertion of said pinion mechanism after the two retractor arms are at least partially assembled with bearing 24 simultaneously engaged within slot 501 of rack bar 5. When the pinion member 63 is engaged with the rack teeth 51, the pinion mechanism 6 is axially retained but free to rotate within the crank housing 42, throughout the open range of the retractor spreader arms 3 and 4.

As illustrated in FIG. 3, the spacer element 22 serves to offset the two ball bearings 24 away from the underside face 422 of the crank housing 42, such that only the cylindrical surface of the outer race 241 engages with the slider slot 501 of linear rail 50. In the illustrated example, the side surfaces of the bearing and nut element 23 do not contact or rub against the sides of slider slot 501, tending to achieve only substantially frictionless and normalized sliding of the retractor arms when the bearing outer race 241 rolls within the slider slot 501. This configuration also results in the load-reducing and load-normalizing mechanism 20, in the preferred nature of a ball bearing, being ergonomically stowed within the said slider slot 501 throughout the entire open range of the retractor spreader arms 3 and 4.

Advantageously, the two ball bearings 24 remain integral with the crank housing 42, and do not have to be disassembled for sterilization. The bearing design is of an open configuration; that is, the rolling elements are non-shielded and non-sealed. The open configuration tends to facilitate cleaning of the blood products from the bearing elements prior to sterilization. The bearing design does not require lubrication, tending to ensure inert and sterile environment during cardiac surgery.

Although the first embodiment, as illustrated in FIGS. 1A, 1B and 3, employs an open configuration ball bearing 24 as part of the load-reducing and load-normalizing mechanism 20, other rolling-element-type bearings can also be employed to configure alternative embodiments for the load-reducing and load-normalizing mechanism. FIGS. 4A to 4I illustrate the top cross-sectional half of rolling-element-type bearing variants, about their respective centerlines CL. Suitable bearings may include but are not limited to: (4A) open configuration ball bearing (also the illustrated example in FIGS. 1A); (4B) shielded ball bearing; (4C) sealed ball bearing; (4D) external self-aligning ball bearing; (4E) double row ball bearing; (4F) self-aligning ball bearing; (4G) straight roller bearing; (4H) needle bearing; and (4I) tapered roller bearing. In these figures, the bearing outer race is generically referred to as OR, the inner race as IR, and the complement of rolling elements as RE. FIG. 4J illustrates a flanged journal bearing.

The sealed ball bearing, illustrated in FIG. 4C, can be either a dry non-lubricated cartridge which is limited in the number of uses to which it can be put, or a self-contained lubricated cartridge which either resists sterilization for repeated uses or is replaced after every surgery.

Figure 5:
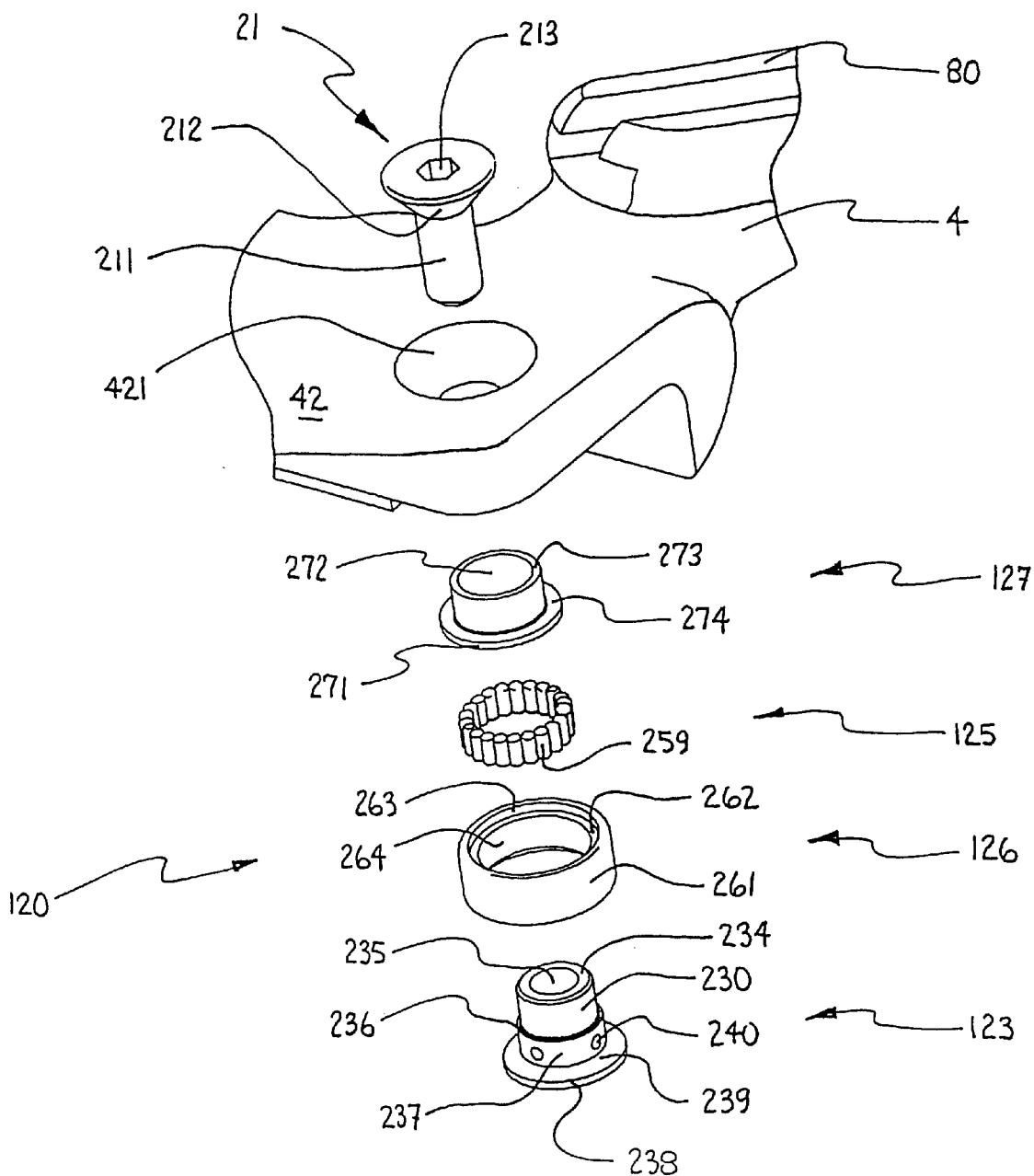
FIG. 5 is an enlarged exploded view illustrating a second embodiment of a load-reducing and load-normalizing mechanism for the sternum retractor of FIG. 1A, in the nature of a needle bearing.

FIG. 5 illustrates the second embodiment 120 for the load-reducing and load-normalizing mechanism, in the nature of an open configuration needle bearing. The spreader arms 3 and 4, the pinion mechanism 6 and the rack bar 5 are the same as in the first embodiment, and are not shown in FIG. 5. FIGS. 6A–6D illustrate assembled views of this second embodiment without the crank housing 42.

The load-reducing and load normalizing mechanism 120 is comprised of inner hub 123, outer race 126, retainer 127, screw element 21, and a plurality of cylindrical pins 259 serving as the bearing rolling elements. The annular gap between the inner diameter 264 of the outer race 126 and the outer diameter of inner race 237 is sized as a function of the desired number and diameter of pins 259 to configure an annular cluster 125 (FIG. 6C) when said cylindrical pins are assembled between said outer race and inner hub. Slight circumferential gaps result between the cylindrical pins 259 when assembled as a cluster 125 tending to facilitate the rotation of outer race 126 about the inner hub 123. Cylindrical pins 259 can be classified as to their diameter size in order to allow for a selective close tolerance assembly of cluster 125 radially retained within annular gap formed between inner diameter 264 and inner race 237.

Guiding diameter 230 serves as a guide for the pilot diameter 272 during the installation of retainer 127 onto inner hub 123. The diametrical fit between guiding diameter 230 and pilot diameter 272 is preferably an interference fit. Swaging or stacking can also be implemented between the retainer 127 and receiving portion of inner hub 123, to further secure this assembly from disengagement. Cluster 125 is limited in axial movement between hub flange 239 and retainer flange 274, which serve to axially retain the said cluster once the retainer flange 274 rests up against abutment face 236 of inner hub 123. Axial movement of cluster 125, or any of the cylindrical pins 259, is limited by gap 267 (FIG. 6D). Outer race 126, although free to rotate, is also limited in axial movement between hub flange 239 and retainer flange 274. Axial movement of outer race 126 is limited by axial gap 266 Axial gap 266 is preferably smaller than axial gap 267.

Retainer 127 being fully seated against abutment face 236 results in an axial gap between recess face 234 of inner hub 123 and bearing face 273. The entire load-reducing and load-normalizing mechanism 120 is secured to the crank housing 42 by screw element 21 which places retainer 127 in compression and in contact with crank housing underside surface 422 (FIG. 3) through its bearing face 273 when threaded body 211 engages inner hub internal thread 235. Guiding diameter 230 of inner hub 123 is in tension.

Retainer 127 serves to offset outer race 126 from underside surface 422 and situate said outer race within slot 501 such that preferably only the outer diameter 261 contacts and rolls along lateral side faces of slot 501, as the spreader arm 4 moves along rack bar 5 through the rotation of pinion mechanism 6. Cylindrical pins 259 rotate about their axis and roll as a cluster between inner race 237 of non-rotating inner hub 123 and inner diameter 264 of rotating outer race 126. $F_{BRG}$ is transferred from spreader arm 3, more precisely lateral face of slot 501 of rack 5, to outer race 126, to cylindrical pins 259, to inner race 237, and to crank housing 42 of spreader arm 4 through retainer 127 clamped by threaded interface between screw element 21 and inner hub 123.

Inner hub 123 is preferably configured with a hollow center to provide internal thread 235 for engagement with screw element 21, to provide a passage to cylindrical pins 259 for cleaning fluid, and to provide a hex drive socket 213 for fastening purposes, preferably manufactured through a broaching operation.

Subsequent to use in surgery, a flushing or cleaning solution may be injected through the center of inner hub 123, preferably with a standard syringe whose needle tip has been removed, and that interfaces with countersink surface 215. The solution then passes radially outwards through a series of radial passages 240 where it enters the plenum created between inner hub 123 and outer race 126, which houses the cylindrical pins 259. The cleaning solution is capable of circulating freely between any circumferential space between said pins. While injecting cleaning solution through the center of inner hub 123, the outer race 126 can also be rotated with the other hand to set the bearing rolling elements into motion and assist in dislodging any blood products or other contaminants to be flushed. The cleaning solution is channeled through mechanism 120 via the following series of passages: the axial gap 267 resulting between the height of pins 259 and the assembled dimension between retainer flange 274 and hub flange 239; the axial gap 266 resulting between the axial stepped width 262 of bearing outer race 126 and the assembled dimension between retainer flange 274 and inner hub flange 239; annular gap 265 and 268 resulting from inner recess diameter 263 of outer race 126 and retainer flange diameter 271 or hub flange diameter 238.

This results in the load-reducing and load-normalizing mechanism 120 in the nature of a needle bearing, capable of being flushed from blood product or other contaminants prior to sterilization without having to disassemble any of the constituent components.

The material of components comprising the load-reducing and load normalizing mechanisms 20 and 120, is preferably stainless steel, or other non-oxidizing, non-corroding materials when exposed to the environments of surgery, sterilization and the like. If a stainless steel material is selected, one with a tempering temperature above the range of temperatures seen during steam sterilization or dry heat sterilization cycles is preferable to avoid embrittlement of the component material.

Figure 7:
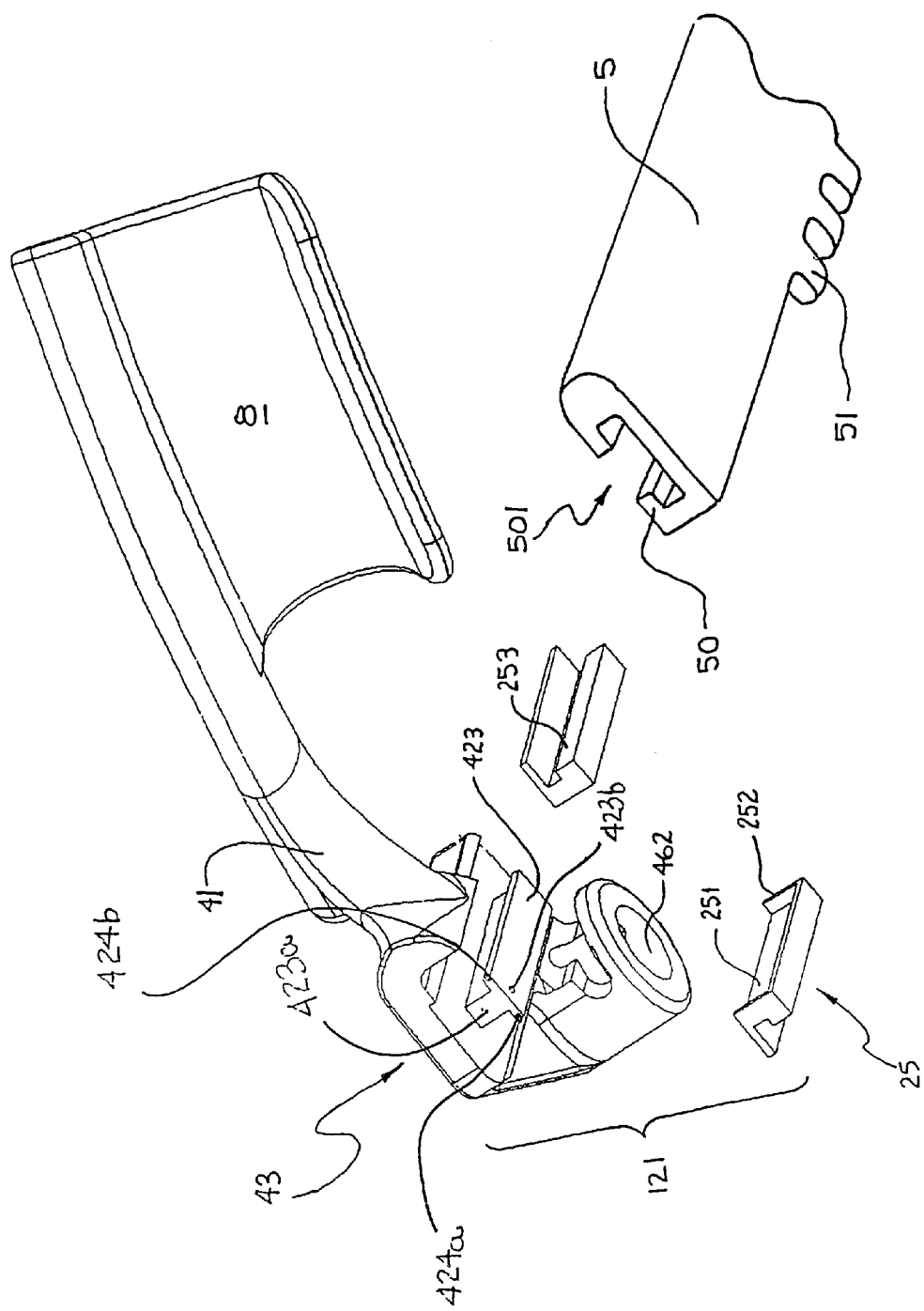
FIG. 7 is an exploded perspective view illustrating a third embodiment of the load-reducing and load-normalizing mechanism for the sternum retractor of FIG. 1A, in the nature of a sliding member arrangement.

FIG. 7 illustrates a third embodiment according to this invention. The rack bar 5 and pinion mechanism 6 (not shown) are the same as in the previous embodiment and are combined here with a movable spreader arm 41. A load-reducing and load-normalizing mechanism 121 is comprised of a sliding member 25 which replaces the rolling element bearing system in the first and second embodiments. The underside of the crank housing 43 is configured with a protruding key feature 423, which can be integral with the retractor arm or demountable. The key feature 423 preferably consists of a depending member which is substantially transversely disposed with respect to spreader arm 41 and has a web portion 423a and flange portion 423b to form a substantially T-shaped cross-section. The flange portion 423b defines two longitudinally disposed lips 424a, 424b extending opposite one another from the web portion 423a. Two corresponding components 252, 253 of sliding member 25 are provided, each being configured with a backface slot 251 which mates with substantially half the outer profile of key feature 423. Namely, each of the components 252, 253 mates with a longitudinal face of web portion 423a and one of lips 424a, 424b. When assembled onto key feature 423, the outside profile of the components 252, 253 mates in sliding engagement with slot 501 in the rack bar, which in this embodiment acts like a keyseat slot.

When inserted into slot 501, the two components 252, 253 of sliding member 25 are restrained transversely by said slot, and are also retained axially relative to key feature 423 through their engagement of backface slot 251. Consequently, the sliding member 25 moves together with the retractor arm 41 relative to rack bar 5 within slot 501, to provide for substantially frictionless sliding motion and deployment of the retractor.

With most retractors being fabricated in stainless steel, the material of the sliding member 25 is preferably teflon, plastic, polymer, or any other material well-suited to mate with the retractor material to provide a substantially frictionless translation of one retractor arm relative to the rack and to the other retractor arm. With lightweight aluminum retractors, the sliding member 25 not only reduces sliding friction, but also acts as a wear-resistant bushing to prevent wear between sliding aluminum parts. If the material of sliding member 25 cannot be sterilized, it must be replaced after every surgery.

If the sliding member 25 is fabricated with a process similar to plastic injection, the two halves can be joined through a flexible hinge arrangement, preferably along one of the backface perimeter lengths 252. This would enable the two halves to be angularly opened relative to each other, fitted and then closed over key feature 423 with contact along perimeter 252.

In this third embodiment, feature 423 covered by sliding member 25 forms a T-shaped key which slides within a T-shaped keyseat slot 501 in the rack bar 5. Other variations of key and keyslot geometry are possible which do not depart from the spirit of this invention, such as: L-shape, dovetail, firtree and others apparent to those skilled in this art.

Figure 8:
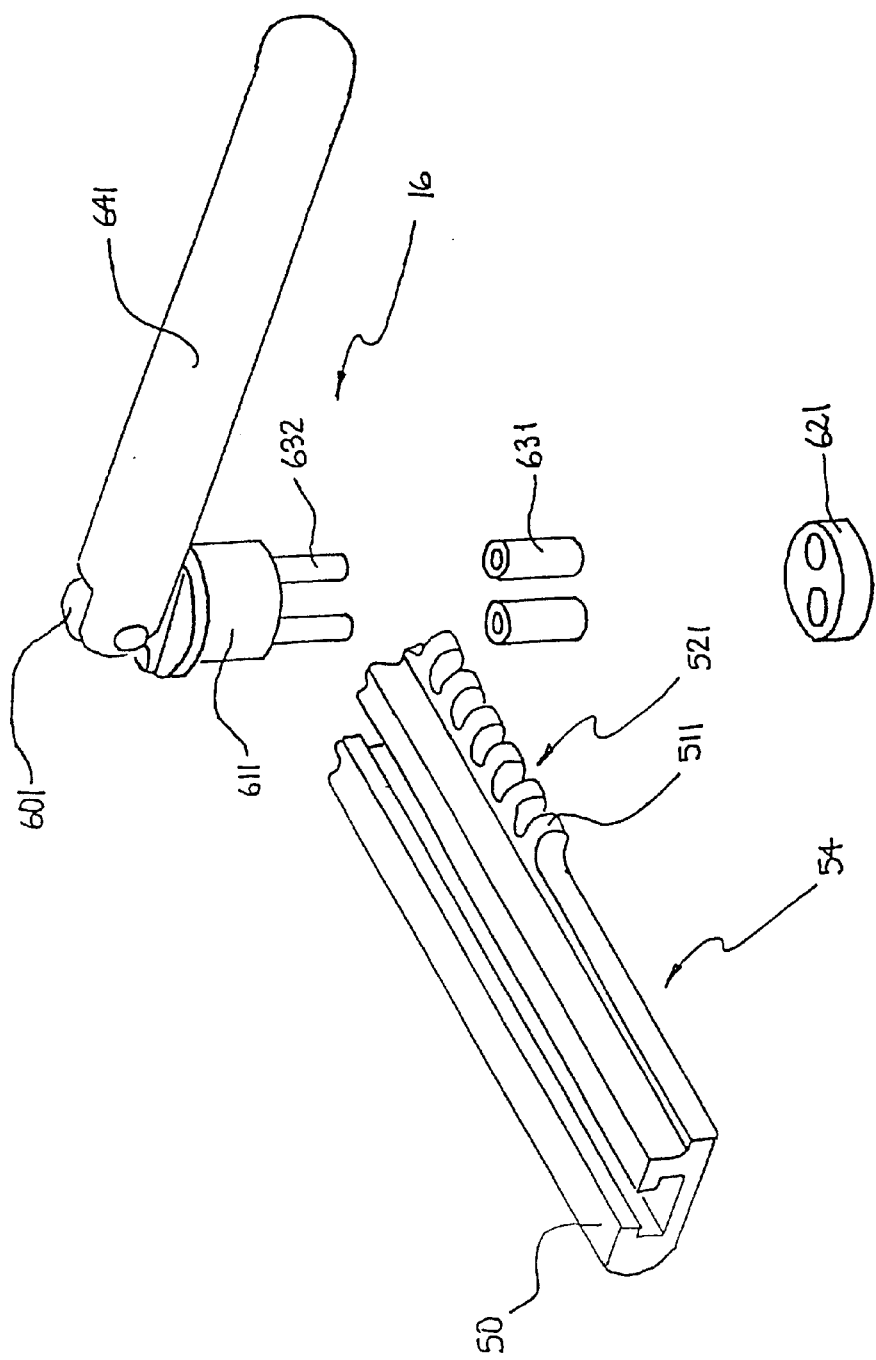
FIG. 8 is an exploded perspective view illustrating a fourth embodiment according to this invention, comprising a friction-reducing member for the pinion mechanism of the sternum retractor of FIG. 1A.

FIG. 8 illustrates a fourth embodiment according to the present invention. In order to reduce the friction force $Ff_{PINION}$, and consequently the force $F_{SURGEON}$ and torque $M_{SURGEON}$ the surgeon must apply at the crank handle 641, a friction-reducing member 631 is introduced as part of the pinion mechanism 16.

In a first configuration of this fourth embodiment, feature 631 is a substantially cylindrical sleeve which is press-fit (interference fit) onto pinion member 632. With the rotation of the crank 641, the outer surface of sleeve feature 631 rotates as it slides relative to the rack tooth 511 surface. The material of the sleeve is either teflon, plastic, polymer, or any other material well-suited to provide substantially frictionless movement of the pinion relative to the rack. The sleeve tends not only to reduce friction between the pinion member 632 and the rack tooth 511, but also to reduce the wear at this interface. In most prior art retractors, the pinion member and rack tooth are made of similar materials, which is not ideal for minimizing wear. The sleeve can also be replaced by a friction-reducing and wear-reducing coating of dissimilar material properties to the rack tooth, like a plasma coating or ion implantation coating. The spacing 521 between rack teeth 511 may be modified accordingly to account for introduction of sleeve feature 631.

In an alternative configuration of this fourth embodiment, friction-reducing member 631 can act as a journal element. Journal element 631 is assembled onto pinion member 632 with a loose fit. With the rotation of the crank 641, the inner surface of journal element 631 slides and rotates relative to the outer surface of pinion member 632, and the outer surface of journal element 631 rolls on the surface of rack tooth 511. The friction-reducing member 631 in the nature of a journal element can also be replaced by a more conventional needle bearing or other bearing types as illustrated in FIG. 4.

In both these configurations of the fourth embodiment, the friction-reducing member 631 preferably lends itself to repeated sterilization, or it must be replaced after every surgery or at limited intervals.

FIG. 9 illustrates the fifth embodiment according to this invention. In order to reduce the friction force $Ff_{CRANK}$, and consequently the force $F_{SURGEON}$ and torque $M_{SURGEON}$ the surgeon must apply at the crank handle 642, a friction-reducing member 613 is introduced to act between the pinion journal 612 and counterbore recess 463 of crank housing 44. In the first configuration of this embodiment, the friction-reducing member 613 is a ball bearing which can either be press-fit on the outer diameter of the top pinion journal 612 to form an insertable assembly with the pinion mechanism 116, or press-fit on the inner diameter of a counterbore recess 463 to form an assembly with the crank housing 44. Other bearing types as illustrated in FIG. 4 can also be used in place of the ball bearing friction-reducing member 613.

In an alternative configuration of this fifth embodiment, the friction-reducing member can be a cylindrical sleeve or journal element (not shown) that is preferably assembled with at least one loose fit, either with the pinion journal 612, the counterbore recess 463 or the bore diameter in crank housing 44. The friction-reducing member in the nature of a journal element may be made of low-friction material compatible with the material of pinion mechanism, preferably teflon, plastic, or a polymer material. Rotation of the crank 642 is easier and smoother (lower $F_{SURGEON}$ and $M_{SURGEON}$) due to the substantially frictionless rotational slip interface resulting between the journal element and 612, between the journal element and the bore diameter in crank housing 44 or between the journal element and counterbore recess 463.

Similarly, a second friction-reducing member 613 can also be incorporated between the bottom pinion journal 622 and the bore diameter in crank housing 44. The friction-reducing member 613 acts not only to reduce friction between a portion of the pinion mechanism 116 and the crank housing 44, but also to reduce the wear at this interface.

FIGS. 10A to 10D illustrate the sixth embodiment according to this invention, which seeks to improve the deployment of chest retractors by providing a locking mechanism 90, 91, or 92 capable of achieving a substantially stable open retractor position, throughout the entire variable range of open retractor arm positions.

The pinion mechanism 9 usually consists of two pinion members 634 which engage the rack teeth 512 in a variety of orientations depending on the rotation of crank 643 of the pinion mechanism. A substantially stable orientation results when both pinion members 634 are longitudinally aligned and engaged within rack teeth 512. A substantially unstable position results when only one pinion member 634 is engaged with the rack teeth 512, with the most unstable position occurring when both pinion members 634 are transversally aligned relative to rack bar, and only the top pinion member is in contact with the rack teeth (similarly illustrated by pinion member 63 in FIG. 2B). Consequently, along the length of the rack bar 55, there exists discrete settings of retractor arms which are substantially stable, interspersed with relative settings that are substantially unstable. An open retractor usually has a tendency to close slightly from a substantially unstable position to attain the closest substantially stable position.

The present invention provides a retractor that is capable of locking the retractor arms in any desired open position, and does not rely on the discrete orientation of pinion mechanism 9 relative to the rack teeth 512 to achieve stability.

Figure 10A:
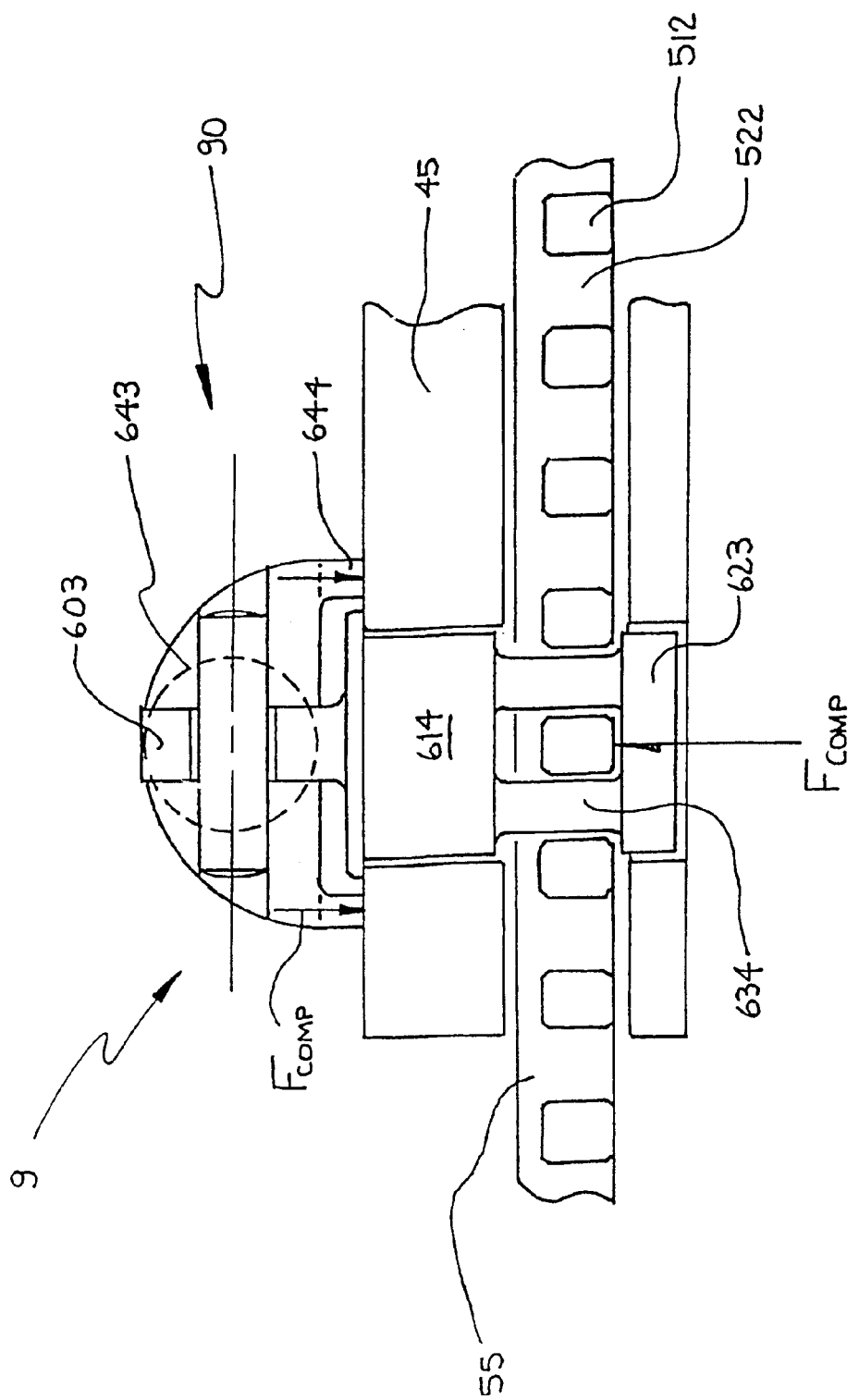
FIG. 10A is a partial cross-sectional view of the sternum retractor of FIG. 1A, showing a sixth embodiment according to this invention, and having a locking mechanism between the crank and pinion mechanism of said retractor.
Figure 10B:
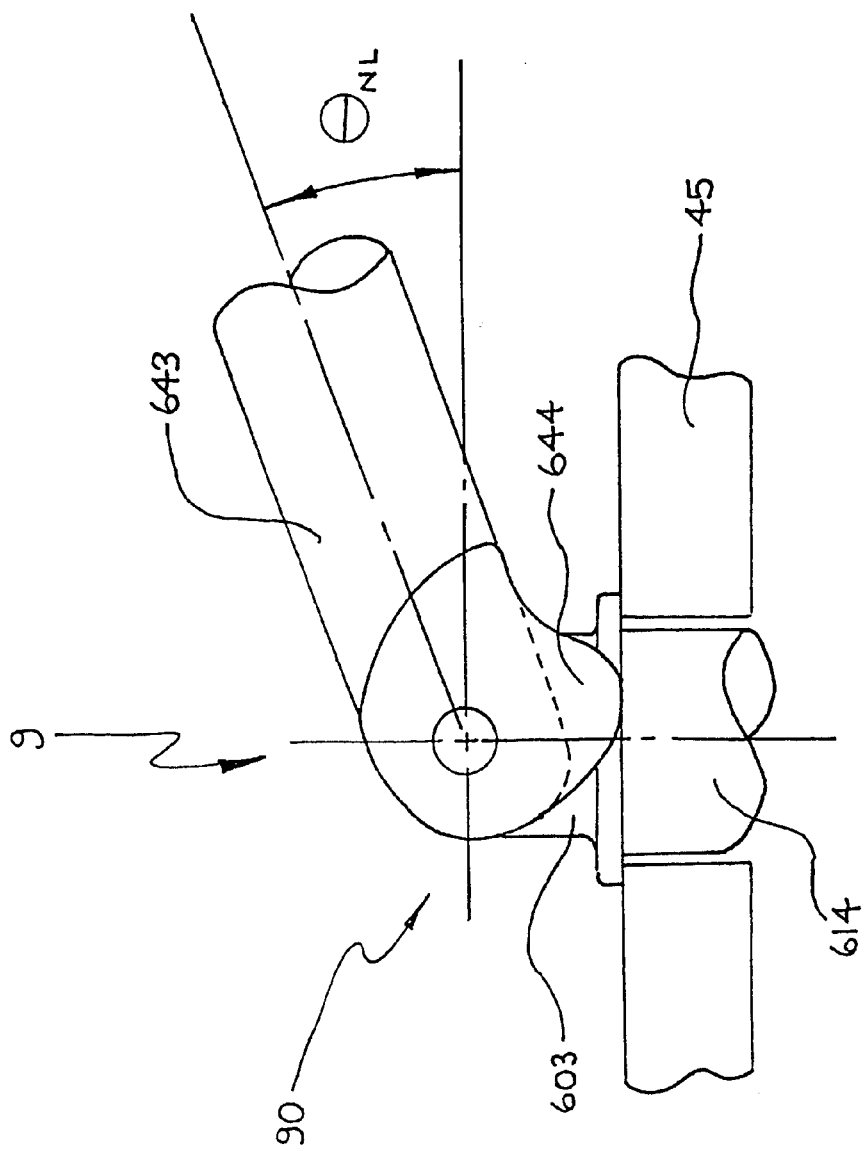
FIG. 10B is a side elevational view of the locking mechanism of FIG. 10A illustrating a cam lock feature.

In the first configuration of this sixth embodiment as illustrated in FIGS. 10A and 10B, the locking mechanism 90 is comprised of a cam lock feature 644. While the retractor is being deployed by the rotation of the crank 643, said crank forms a minimum non-locking angle $\theta_{NL}$ relative to the top surface of crank housing 45 (FIG. 10B), to provide clearance for the surgeon's or assistant's hand and fingers during cranking. Once the desired open position of retractor arms 3 and 4 is achieved, the crank 643 is stowed by pivoting it downward through the angle $\theta_{NL}$ thereby engaging the cam lock feature 644. The cam lock feature 644 imposes a compressive force $F_{COMP}$ acting on the top surface of the crank housing 45, and reacted on the bottom surface of the rack tooth 512 by the bottom pinion journal 623. This motion locks the pinion mechanism relative to the rack, and consequently the two retractor arms in the desired open position.

Figure 10C:
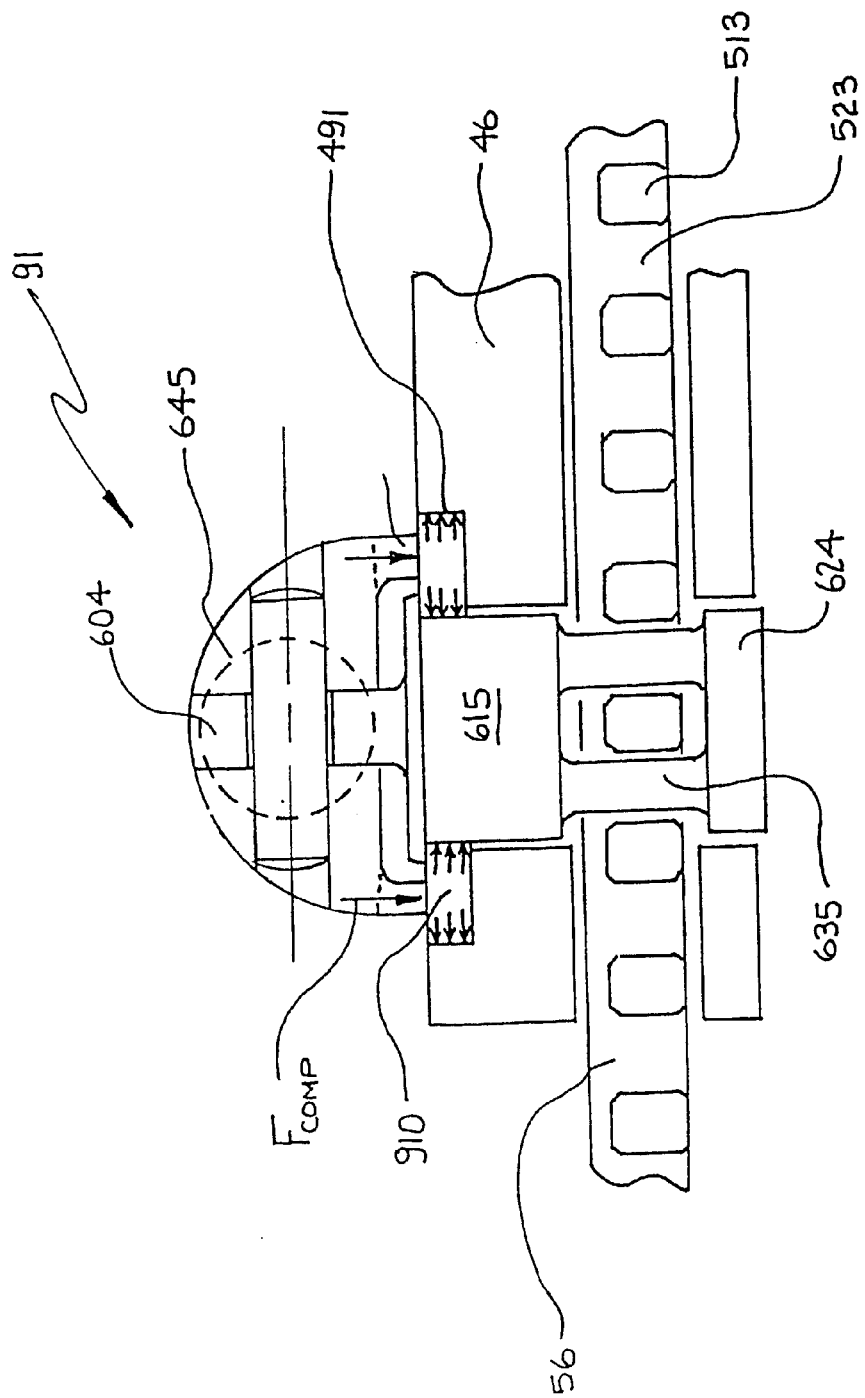
FIG. 10C is a partial cross-sectional view of a first variant to the sixth embodiment of FIG. 10A, illustrating a locking mechanism and hydraulic sleeve feature.

FIG. 10C illustrates a variant to this sixth embodiment whereby the locking mechanism 91 is comprised of a cam lock 646 and a hydraulic sleeve feature 910. The pivoting of the crank 645 through angle $\theta_{NL}$ (as similarly illustrated in FIG. 10B) results in a force $F_{COMP}$ acting on the top surface of the hydraulic sleeve feature 910, which consequently causes an expansion of the outer diameter and a contraction of the inner diameter of the said hydraulic sleeve. A tight fit results between the hydraulic sleeve 910, the top pinion journal 615, and the counterbore recess 491 in the crank housing 46. This motion locks the pinion mechanism relative to the rack, and consequently the two retractor arms, in the desired open position.

Figure 10D:
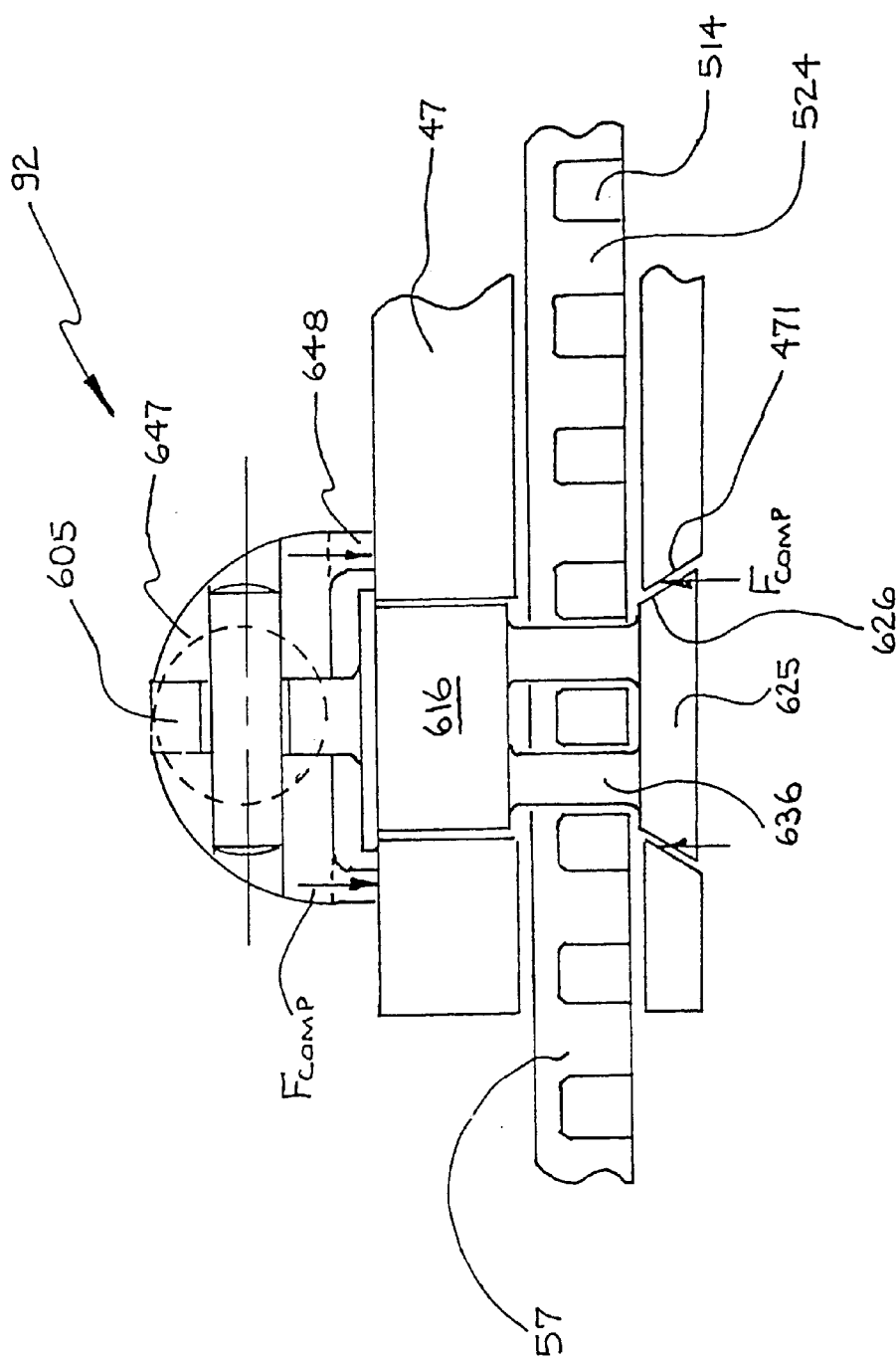
FIG. 10D is a partial cross-sectional view of a second variant to the sixth embodiment of FIG. 10A, illustrating a locking mechanism and wedge feature.

FIG. 10D illustrates a variant of this sixth embodiment where the locking mechanism 92 is comprised of a cam lock feature 648 and a wedge feature 626 on bottom journal pinion 625. The pivoting of the crank 647 through angle $\theta_{NL}$ (as similarly illustrated in FIG. 10B) results in the reaction of $F_{COMP}$ through the wedge feature 626 and the tapered recess 471 in the crank housing 47.

Alternatively, this wedge principle can be applied between the top pinion journal 616 and a tapered recess in crank housing 47.

As well, the wedge principle can be applied between the pinion member 636 and the sides of rack teeth 514, whereby both these features are substantially tapered in profile to achieve a wedging action between them once cam lock feature 648 is deployed.

Figures 11A, 11B:
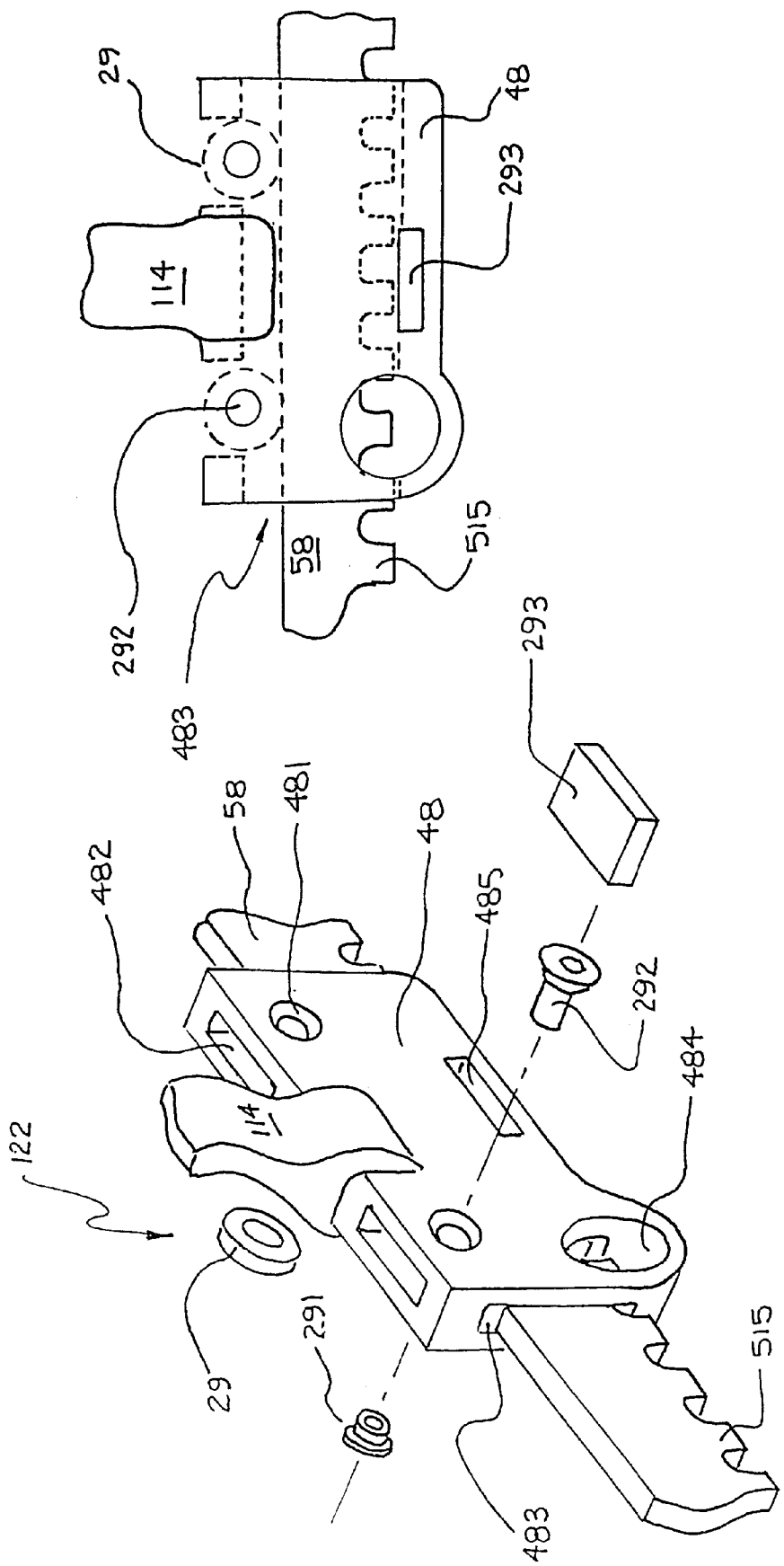
FIG. 11A is a partial perspective view of a seventh embodiment according to this invention, illustrating the retrofit of a load-reducing and load-normalizing mechanism to existing retractors.
FIG. 11B is a partial side elevational view of the seventh embodiment of FIG. 11A.

FIGS. 11A–11B illustrates a seventh embodiment of this invention, whereby the principles of the first, second, and third embodiments are applied to existing retractors as retrofit designs. The load-reducing and load-normalizing mechanism 122 is comprised of at least one rolling element bearing 29. In this example, two bearings 29 are each assembled in slots 482 in the crank housing 48 by a screw element 292 and nut element 291, and at least one sliding member 293 which is also inserted in a slot 485 or sits in a recess within slot 483. Once assembled, the outer race of the bearing 29 and the sliding member 293 extend inwardly into slot 483, and contact respectively with the top of rack bar 58 and rack teeth 515 when said rack is inserted and slides through said slot. As the retractor arm 114 moves relative to the rack bar 58, the rolling of bearings 29 and low-friction slipping at interface with sliding member 293 results in the friction force $Ff_{SLIDER}$ being substantially reduced.

Rolling element bearing 29 can also be replaced by variations as illustrated in FIGS. 4A–4I without departing from the spirit of this embodiment. Bearing 29 can also be replaced with a journal sleeve.

With most retractors being fabricated in stainless steel, the sliding member 293 material is preferably a teflon, plastic, polymer, or any other material well-suited to mate with retractor material to provide substantially frictionless translation of one retractor arm relative to the rack and other retractor arm.

The remaining FIGS. 12A to 12C, 13A, 13B, 14A to 14D, and 15A, 15B illustrate the eighth embodiment according to the present invention. As already illustrated in FIG. 2A, the arcuate blades 7 and 8 of the sternum retractor 1 are advantageously configured with a curvature that tends to minimize the trauma, tearing and excessive retraction of the thoracic structure (labelled "TS" in FIG. 13B) at the extremities of the incision (for instance the topmost extremity thereof labelled "TEI"), for a given desired opening at the mid-length location along the incision where the surgical intervention will most likely be performed.

For the purposes of this present invention, the cylindrical-like configuration is defined as the anatomical configuration of the patient's thoracic structure when the ribcage halves are in integral contact at the sternum prior to a midline sternotomy incision, or immediately adjacent one another after the sternotomy incision and prior to retraction. In both instances, the ribcage is engaged with the patient's spine. After the sternotomy incision, the cylindrical-like configuration implies that the two halves of the incised sternum remain in close proximity, substantially parallel to one another along the incision and substantially in the same orientation with respect to one another as they were prior to the sternotomy incision.

Figures 13A, 13B:
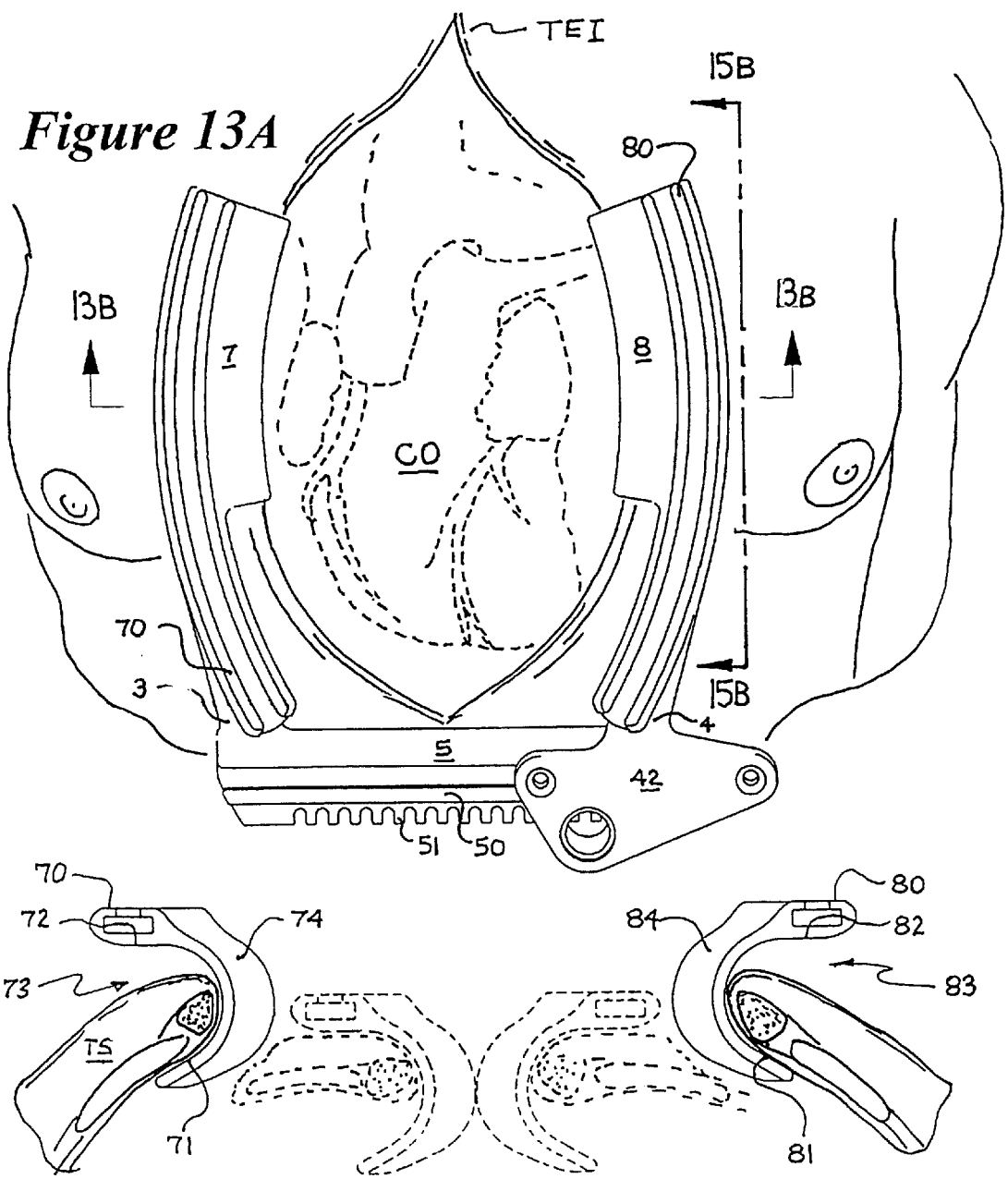
FIG. 13A is a top anterior view of the sternum retractor and the patient's retracted thoracic structure of FIG. 12A, exposing the coronary organs.
FIG. 13B is a partial cross-sectional view through the patient's retracted thoracic structure and the sternum retractor of FIG. 12A, illustrating the engagement of the thoracic structure in its barrel-like configuration with portions of the arcuate blades of the retractor which are adjacent lower longitudinal edges thereof.
Figures 15A, 15B:
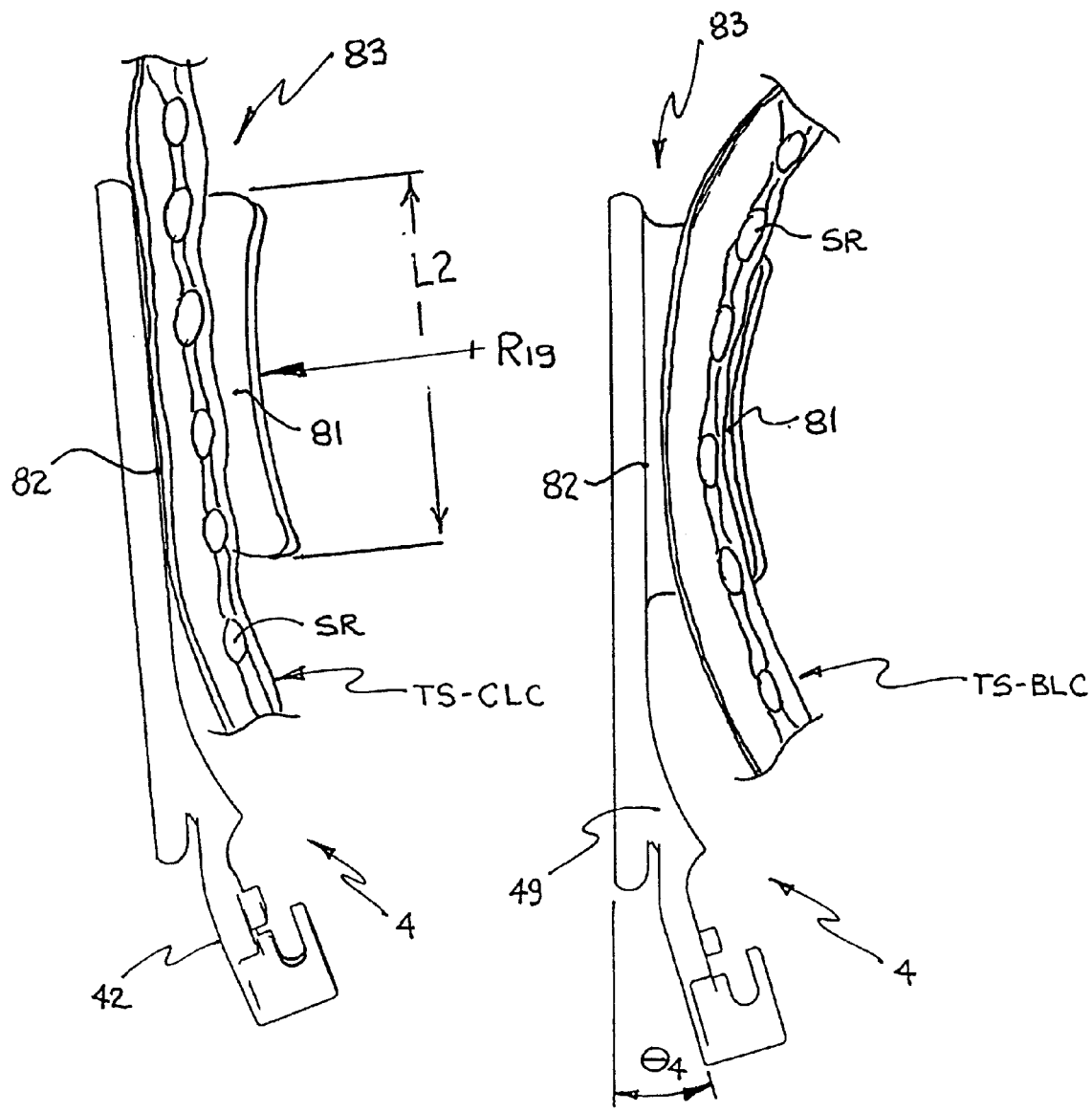
FIG. 15A is a partially sectional view through the sternum retractor of FIG. 1A and the patient's thoracic structure in its cylindrical-like configuration prior to retraction.
FIG. 15B is a sectional view through the sternum retractor of FIG. 1A and the patient's thoracic structure in its barrel-like configuration after retraction.

FIG. 2A shows an anterior aspect of the retracted thoracic structure exposing the coronary organs. FIGS. 12A to 12C and FIG. 15A illustrate the engagement of the patient's thoracic structure with the sternum retractor 1, in cylindrical-like configuration, prior to retraction. FIGS. 13A to 13B and FIG. 15B illustrate the engagement of the patient's thoracic structure with the sternum retractor 1, in barrel-like configuration, after retraction. The pinion mechanism 6, the screw elements 21, and part of the rack bar are not shown in these figures.

As seen from above in FIGS. 12A, 13A and 14A, the arcuate blades 7,8 and arcuate retractor spreader arms 3,4 are defined by radius R1 in a plane P1 (FIG. 12B) through the innermost portion of facing blades 7 and 8, and by a radius R2 in plane P2 (FIG. 12B) defining the longitudinal centre-line of arcuate rails 70 and 80. Preferably, but not necessarily, the center of R1 and R2 are on the same axis of revolution defining their curvature. These radii R1 and R2 are related to the overall length L1 of the spreader arm. Proportional scaling of these dimensions can take place for smaller and larger retractors as a function of L1. The arcuate circumferential length ARC1 (FIG. 14A) of blades 7 and 8 can also be varied proportionally for a constant R1, R2 and a given spreader arm length L1, if shorter blades are desired as thoracic structure engaging members, for instance.

Blades 7 and 8 are in contact at their free terminal ends when the retractor is closed, as at contact points 79, 89. Contact points 79 and 89 lie on plane P1 (FIG. 12B). At the closest location to the rack bar 5, a gap G8 (FIG. 12A) between the blades 7 and 8 results. This achieves a rounded bowed profile in plane P1. In other words, the blades 7, 8 being are in contact with one another at contact points 79, 89, then progressively extend apart from one another to a maximum gap G7 as rack bar 5 is approached, and finally resume their convergence at the closest location to rack bar 5, forming gap G8. This configuration tends to facilitate insertion of the said retractor, more specifically the said blades, by inserting the portion of the blades 7 and 8 which are in contact into the base of the sternotomy incision closest to the abdomen, and then by longitudinally sliding the retractor towards the top of the sternotomy incision towards the patient's head with blades 7 and 8 engaged with opposing halves of the sternum and thoracic structure. This motion progressively moves the sternal halves apart to create the maximum opening G7 at approximately the mid-length location along the incision prior to mechanical retraction of the retractor. This mid-length location along the incision is also usually the location where the maximum retraction of the thoracic structure is preferably sought for exposure during surgery, and also where the maximum barrelling of the thoracic structure is likely to occur, as explained below.

FIG. 12B is a sectional view through the sternum retractor 1 and patient's thoracic structure at section line 12B—12B of FIG. 12A. The coronary organs are not shown. The sternum retractor 1 is inserted into the sternotomy incision but is not yet retracted. Gap G7 illustrates the slight spacing between the blades at this section location, resulting by virtue of the engagement of concave surface 73 and 83 of arcuate blades 7 and 8 with the sternal halves of the thoracic structure.

Prior to retracting, the thoracic structure is still in its cylindrical-like configuration; that is, both halves of the incised sternum are disposed substantially parallel to one another along the sternotomy incision. The two halves of the thoracic structure substantially maintain their anatomical orientations with respect to each other except for the lateral widening of the sternum halves, to a varying degree along the arcuate blades 7 and 8, which occurs subsequent to sternum retractor 1 being engaged with the thoracic structure. At this point, the top surface of the thoracic structure, on either half of the sternotomy incision, contacts the substantially planar underside surface 72 and 82 of the retractor spreader arms 3 and 4 (FIG. 12B). At the location closest to the sternotomy incision, this top surface of the patient's thoracic structure is in substantially parallel orientation with said underside surfaces 72 and 82.

The foregoing is further illustrated in FIG. 15A, which is a partially sectional view through the patient's thoracic structure with the sternum retractor 1 engaged. The view is at section plane 15A—15A (FIG. 12A), which is located just left of the spreader arm 4 and perpendicular to the bisector of arcuate circumferential length ARC1. The patient's thoracic structure is in its cylindrical-like configuration and the top surface of the thoracic structure is in substantial contact with the planar underside surface 82 of spreader arm 4. The thoracic structure is schematically represented with sectioned ribs (labelled SR). This example illustrates that the thoracic structure is not in contact with the surfaces 71 and 81 of blades 7 and 8 that are adjacent the free longitudinal edges thereof. The degree of non-contact with the extension portions 71 and 81 will depend on a patient's specific anatomy and size of retractor selected. In this example, the sternum retractor is illustrated to engage with the sternum adjacent to rib nos. 2, 3, 4, and 5 (anatomical numbering). The sternum retractor can be placed longitudinally along the sternotomy incision to engage adjacent to other ribs, such as rib nos. 3 to 6 (anatomical numbering) for instance.

FIGS. 14B to 14D illustrate sectional views along the arcuate spreader arm 4, through the portion of the spreader arm which is configured with an underlying blade 8. The arcuate portions of opposing spreader arm 3 and blade 7 are preferably mirror image configurations of arcuate portions of spreader arm 4 and blade 8 about a plane normal to the longitudinal axis of rack bar 5. FIG. 14B is the sectional view along 14B—14B (FIG. 14A), which is adjacent the mid-arc length of the blade 8. This section through blade 8 is preferably defined by a radius R11 and two extensions L31 and L32. Each extension commences generally tangent to R11 and divergently extends away from the center of R11 resulting in an angle $\theta_1$ between said extensions. The first extension L31 defines a portion of the arcuate spreader arm 4 containing arcuate rail 80. The other extension L32 defines a portion of blade 8 which depends furthest away from the spreader arm and comprises a portion of the free longitudinal edge of the blade. The extensions L31 and L32 are preferably 0.6 to 0.8 times as long as radius R11. This defines the profile of the concave surface 83 at section 14B—14B.

The profile of the convex surface 84 (and similarly 74) is defined by offsetting the concave profile 831 by thickness t for uniform thickness blades. Alternatively, the blade thickness can be variable from the extending-most portion of the blade to the portion of the blade joining the spreader arm 4. The concave surface 83 of the blade 8 yields a concave profile 831, 832, 833 when sectioned respectively at locations 14B—14B, 14C—14C, and 14D—14D. Concave surface 83 also yields a concave profile at any other section therebetween. The convex surface 84 of the blade 8 yields a convex profile 841, 842, 843 when sectioned respectively at locations 14B—14B, 14C—14C, 14D—14D. Convex surface 84 yields a convex profile at any other section therebetween.

FIGS. 14C and 14D are sectional views adjacent the longitudinal extremities of blade 8. These sections are defined by R12 and R13, where R12 and R13 are preferably equal to R11 or more preferably slightly larger than R11 (1.1 to 1.2 times R11). They are also defined by $\theta_2$ and $\theta_3$ between extensions L41 and L42, and L51 and L52, respectively, and where $\theta_2$ and $\theta_3$ are each larger than $\theta_1$ by 5 to 10 degrees. The configuration of blade 8 at location 14C—14C and 14D—14D is preferably, but not necessarily, the same.

The portions of the blade 8 which span section 14B—14B to section 14C—14C, and which span section 14B—14B to section 14D—14D, are defined by progressively larger R11, or progressively larger $\theta_1$, or both, to attain the blade profile of the extremity locations. Preferably, this progression is achieved with a smooth transition. This construction tends to result in the extending-most portion of blade 8 being capable of conforming to a substantially cylindrical surface defined by radius R19 (FIG. 15A), where R19 is best defined in a plane P3 (not shown) which is normal to plane P2, which contains section plane 15A—15A and which bisects the arcuate circumferential length ARC1. A larger R19 results if R12 and R13 are of a dimension closer to dimension R11, or if angles $\theta_2$ and $\theta_3$ are closer in value to angle $\theta_1$. A smaller R19 results if R12 and R13 are of a dimension greater than dimension R11, or if angle $\theta_2$ and $\theta_3$ are larger in value than angle $\theta_1$.

The smaller the value of R19, then the greater the curvature, and the greater the barrelling effect imposed on the sternal halves during retraction for a given linear blade length L2 shown in true view in FIG. 15A. The barrelling effect produces the result that the middle portion of the incised sternum extends upwardly and laterally outwardly more than the extremities of the incised sternum relative to the cylindrical-like configuration of the thoracic structure prior to retraction. This promotion of a barrelling effect in the patient's thoracic structure during retraction is expected to induce less trauma to the tissue surrounding the sternotomy incision. First, as previously explained, the midportions of the retractor blades 7, 8 are each characterized by a free terminal edge which is disposed higher than the corresponding edge of each of the terminal longitudinal portions of the blades, such that the tissue and bone structure adjacent the two endpoints of the incision will not be urged upwardly to the same degree as the tissue and structure adjacent the midpoint of the incision. Second, as previously explained, the midportions of each of the retractor blades 7, 8 are further apart than are the terminal longitudinal portions thereof at any stage of retraction, such that the tissue and bone structure adjacent the two endpoints of the incision will not be urged apart to the same degree as the tissue and bone structure adjacent the midpoint of the incision.

In a specific example of a chest retractor for patients with a smaller size thorax, the preferred blade 8 (and by mirror image similarity blade 7) and spreader arm 4 (and by mirror image similarity arm 3) definition is as follows: L1=6.25 in., R1=5.875 in., R2=7.0 in., R3=6.625 in., R11=0.625 in., R12=0.680 in., $\theta_1$=30 degrees, $\theta_2$=37.5 degrees, $\theta_3$=36 degrees, L31=L41=L51=0.375 in., L32=0.500 in., L42= 0.650 in., L52=0.595 in., R19=5.00 in., t=0.125 in, ARC1= 30 degrees.

In another specific example of a chest retractor for patients with a larger size thorax, the preferred blade 8 (and by mirror image similarity blade 7) and spreader arm 4 (and by mirror image similarity arm 3) definition is as follows: L1=8.625 in., R1=7.625 in., R2=8.75 in., R3=8.375 in., R1=0.625 in., R12=0.680 in., R13=0.645 in., $\theta_1$=30 degrees, $\theta_2$=38 degrees 35 minutes, $\theta_3$=35 degrees, L31=L41=L51= 0.375 in., L32=0.500 in., L42=0.700 in., L52=0.600 in., R19=8.125 in., t=0.125 in., ARC1=30 degrees.

In another specific example, R11 may be constant and equal to R12 and R13, and R11 is revolved around the centerline of R3 by an angle of revolution of 30 degrees, to define ARC1 of blade 8 at a distance R1 (FIG. 14A) from the centerline of this revolution. The value of $\theta_1$ in this example progressively increases by 8 degrees to the value of $\theta_2$ and $\theta_3$ from section 14B—14B to the respective extremity sections 14C—14C and 14D—14D. This results in concave surface, like 83, and convex surface, like 84, of blade 8. As illustrated in FIG. 12C through section 14B—14B of FIG. 14A, both these convex and concave surfaces of the blade 8 can be offset by approximately ⅛ of an inch to create a volume $V_{BLADE}$, within which can be configured the most preferred blade design according to the present invention. Although the blade definition has been defined by R1, R3, R11, R12, R13, ARC1, $\theta_1$, $\theta_2$ and $\theta_3$ with reference to a circular geometry, it can also be defined by elliptical geometries or any other spline geometry provided the resultant concave and convex surfaces have boundaries that generally fall within the volume $V_{BLADE}$.

As illustrated in FIG. 13B, when retracted the thoracic structure is in substantial contact with the substantially conical extension portions 71 and 81 of blades 7 and 8, and is substantially free from contact with planar surface 72 and 82. This is also illustrated in FIG. 15B, which is a section view through the thoracic structure at location 15B—15B of FIG. 13A, just left of spreader arm 4. As previously explained, the thoracic structure assumes a barrel-like configuration (labelled "TS-BLC") with the middle portion of the incised sternum extending more upward from the surgical table (not shown) and more laterally outward than the extremities of the incision, and also with respect to its orientation and position when it assumed a cylindrical-like configuration (labelled "TS-CLC" in FIG. 15A) prior to retraction.

FIG. 15B illustrates a bend 49 in the retractor spreader arm 4 (and similarly in spreader arm 3 not shown) which is intended to facilitate the conformance of sternum retractor arms 3 and 4 to the retracted thoracic structure when in its barrel-like configuration. Thus, in tending to keep rack bar 5 close to patient's abdomen, and preferably in contact therewith, the ergonomics of the surgical worksite are expected to see improvement since the rack bar 5 will be generally positioned below the arcuate arms 3, 4 during operation of the retractor. As well, the stability of the sternum retractor relative to a patient's retracted thoracic structure during the surgical procedure should also be enhanced since the rack bar 5 will tend to maintain its contact with the patient's abdomen throughout retraction. A typical bend range for angle $\theta_4$ is 15 to 20 degrees.

As the sternum retractor 1 retracts the patient's thoracic structure, the thoracic structure is displaced from its cylindrical-like configuration to its barrel-like configuration. The sternal halves typically move in a fashion whereby the top surface of the thoracic structure is in substantial contact with the planar underside surface 72 and 82 of retractor arm 3 and 4 at the start of retraction, to the substantial contact of the inside surface of the thoracic structure with the substantially conical extensions 71 and 81 of blades 7 and 8.

The sternum retractor in the embodiments of this invention is preferably designed with totally re-usable components and with assemblies that can be dismantled, if necessary, for ease of sterilization. All components are manufactured in surgical grade stainless steel, titanium or any other re-usable sterilizable material approved for surgical use. However, any number of components can also be made in disposable surgical grade plastics, if the case for disposable components is warranted.

The above description of the preferred embodiments should not be interpreted in any limiting manner since variations and refinements are possible without departing from the spirit and scope of the invention. For instance, while the sternum retractor has been described herein as being comprised of a fixed retractor arm and a movable retractor arm, those skilled in the art will appreciate that the retractor may be provided with two movable arms if desired.

We claim:

1. A surgical retractor for retracting generally opposed body tissue edges away from each other, said retractor comprising:
    an elongated guide member;
    a first spreader arm and a second spreader arm, said first and second spreader arms being mechanically coupled to said guide member so as to be in a generally perpendicular relationship relative to said guide member and in a generally opposed relationship relative to each other, said first and second spreader arms being movable relative to each other along said guide member between a first position wherein said spreader arms are in a substantially adjacent relationship relative to each other and a second position wherein said spreader arms are in a generally spaced apart relationship relative to each other;
    an interfacing member for allowing guided movement of said first spreader arm relative to said guide member and providing a friction-reducing mechanical interface between said first spreader arm and said guide member;
    said interfacing member being mechanically coupled to said first spreader arm and in rolling contact with said guide member as said first spreader arm moves relative to said guide member.

2. A surgical retractor as recited in claim 1 wherein said interfacing member includes an outer race mechanically coupled to said first spreader arm so as to be rotatable about a race rotating axis, said outer race defining a generally annular outer race contacting surface, said outer race contacting surface being in rolling contact with said guide member when said first spreader arm moves relative to said guide member.

3. A surgical retractor as recited in claim 2 wherein said interfacing member further includes an inner race mechanically coupled to said first spreader arm, said inner race defining a generally annular inner race outer surface, said outer race defining a generally annular outer race inner surface, the diameter of said inner race outer surface being smaller than the diameter of said outer race inner surface, said outer race being rotatably mounted over said inner race for rotational movement therebetween about said race rotating axis.

4. A surgical retractor as recited in claim 3 wherein said inner race is fixedly coupled to said first spreader arm and said outer race rotates around said inner race.

5. A surgical retractor as recited in claim 3 wherein said interfacing member further includes a race friction-reducing component mounted between said inner race outer surface and said outer race inner surface for reducing the frictional force between said inner race outer surface and said outer race inner surface when said outer race rotates relative to said inner race.

6. A surgical retractor as recited in claim 5 wherein said race friction-reducing component includes rolling element balls spaced apart circumferentially.

7. A surgical retractor as recited in claim 5 wherein said race friction-reducing component includes a plurality of substantially cylindrical pins, said pins being disposed in a generally annular cluster between said inner race outer surface and said outer race inner surface.

8. A surgical retractor as recited in claim 4 wherein said race friction-reducing component is in fluid communication with a fluid aperture formed on an outer surface of said retractor.

9. A surgical retractor as recited in claim 8 wherein said fluid aperture is formed on an outer surface of said interfacing member and wherein said interfacing member defines a fluid channel extending between said fluid aperture and said race friction-reducing component.

10. A surgical retractor as recited in claim 1 wherein said guide member is provided with a guiding slot, said interfacing member being in rolling contact with said guiding slot.

11. A surgical retractor as recited in claim 2 wherein said interfacing member is configured, sized and positioned so that said outer race contacting surface is the only surface of said interfacing member contacting said guide member; whereby the only type of contact between said interfacing member and said guide member is a rolling contact.

12. A surgical retractor as recited in claim 2 wherein said guide member defines a guide member guiding surface, said guide member guiding surface being provided with a guiding slot, said guiding slot defining a slot rolling surface, said outer race contacting surface being in rolling contact with said slot rolling surface when said first spreader arm moves relative to said guide member.

13. A surgical retractor as recited in claim 12 wherein said outer race is configured, sized and positioned so that said outer race contacting surface is the only surface of said interfacing member contacting said guide member; whereby the only type of contact between said interfacing member and said guide member is a rolling contact at said slot rolling surface.

14. A surgical retractor as recited in claim 2 wherein said guide member is provided with a guiding slot having a generally inverted "T"-shaped cross-section extending longitudinally therein, said guiding slot defining a pair of opposed channel legs extending towards one another each from one of two opposed channel contacting surfaces in a generally perpendicular relationship thereto, said outer race contacting surface being in rolling contact with one of said channel contacting surfaces.

15. A surgical retractor as recited in claim 2 wherein said retractor further includes an actuator for effectuating said guided movement of said first spreader arm relative to said guide member.

16. A surgical retractor as recited in claim 15 wherein said actuator includes rack teeth extending from said guide member, said actuator also including a pinion mechanism pivotally coupled to said first spreader arm, said pinion mechanism including a pinion member, said pinion member being configured, sized and positioned for operatively cooperating with said rack teeth so as to effectuate said guided movement of said first spreader arm relative to said guide member when said actuator is actuated.

17. A surgical retractor as recited in claim 15 wherein said interfacing member further includes an inner race mechanically coupled to said first spreader arm, said inner race defining a generally annular inner race outer surface, said outer race defining a generally annular outer race inner surface, the external diameter of said inner race being smaller then the internal diameter of said outer race, said outer race being rotatably mounted over said inner race for rotational movement therebetween about said race rotating axis; said guide member defining a guide member guiding surface and an adjacent guide member actuating surface, said guide member guiding surface being provided with a guiding slot, said guiding slot defining a slot rolling surface, said actuator including rack teeth extending from said guide member actuating surface, said actuator also including a pinion mechanism pivotally coupled to a crank housing, said first spreader arm and said inner race being fixedly attached to said crank housing, said pinion mechanism including a pinion member, said pinion member being configured, sized and positioned for operatively cooperating with said rack teeth so as to effectuate said guided movement of said first spreader arm relative to said guide member, said crank housing being configured and sized so as not to contact said guide member; whereby the only contacts between said guide member and components of said retractor are the contacts between said pinion member and said rack teeth and the contact between said outer race contacting surface and said slot rolling surface.

18. A surgical retractor as recited in claim 16 wherein said retractor further includes a pinion-friction-reducing means for reducing the frictional force between said pinion member and contacting rack teeth.

19. A surgical retractor as recited in claim 18 wherein said pinion-friction-reducing means includes a pinion sleeve rotatably mounted on said pinion member, said pinion sleeve being rotatable about a sleeve axis when said pinion sleeve rolls on the outer surface of said contacting rack teeth.

20. A surgical retractor as recited in claim 16 wherein said pinion mechanism is pivotally coupled to a crank housing, said pinion member extending from a pinion journal, said crank housing being provided with a port defining a cylindrical port surface, said pinion journal being configured for rotating within said port; said retractor being further provided with a journal-friction-reducing means for reducing the frictional force between said pinion journal and said port surface.

21. A surgical retractor as recited in claim 20 wherein said journal-friction-reducing means includes a ball-bearing positioned intermediate to at least a section of said pinion journal and said port surface.

* * * * *